(12) United States Patent
Karkar et al.

(10) Patent No.: US 8,083,522 B2
(45) Date of Patent: Dec. 27, 2011

(54) METHOD FOR TOOTH IMPLANTS

(75) Inventors: Issa George Karkar, Burlingame, CA (US); Huafeng Wen, Redwood City, CA (US)

(73) Assignee: Inpronto Inc., San Francisco, CA (US)

( * ) Notice: Subject to any disclaimer, the term of this patent is extended or adjusted under 35 U.S.C. 154(b) by 338 days.

(21) Appl. No.: 12/260,323

(22) Filed: Oct. 29, 2008

(65) Prior Publication Data

US 2010/0105009 A1  Apr. 29, 2010

(51) Int. Cl.
*A61C 8/00* (2006.01)
*G05B 11/01* (2006.01)
(52) U.S. Cl. .......................................... 433/173; 700/98
(58) Field of Classification Search .............. 433/172, 433/173, 215; 700/98
See application file for complete search history.

(56) References Cited

U.S. PATENT DOCUMENTS

| | | | |
|---|---|---|---|
| 5,360,446 A | 11/1994 | Kennedy |
| 5,587,912 A | 12/1996 | Andersson et al. |
| 6,053,733 A | 4/2000 | Aspichueta et al. |
| 6,616,444 B2 | 9/2003 | Andreiko et al. |
| 6,772,026 B2 | 8/2004 | Bradbury et al. |
| 6,846,179 B2 | 1/2005 | Chapouland et al. |
| 6,915,178 B2 | 7/2005 | O'Brien et al. |
| 7,029,275 B2 | 4/2006 | Rubbert et al. |
| 7,153,135 B1 | 12/2006 | Thomas |
| 7,156,655 B2 | 1/2007 | Sachdeva et al. |
| 7,185,206 B2 | 2/2007 | Goldstein |
| 7,220,122 B2 | 5/2007 | Chishti |
| 7,234,937 B2 | 6/2007 | Sachdeva et al. |
| 7,245,977 B1 | 7/2007 | Simkins |
| 7,322,824 B2 | 1/2008 | Schmitt |
| 7,328,077 B2 | 2/2008 | Dubrin et al. |
| 7,331,786 B2 | 2/2008 | Poirier |
| 7,333,874 B2 | 2/2008 | Taub et al. |
| 7,383,198 B1 | 6/2008 | Sepe |
| 2002/0013636 A1 | 1/2002 | O'Brien et al. |
| 2002/0180760 A1 | 12/2002 | Rubbert et al. |
| 2003/0109784 A1 | 6/2003 | Loh et al. |
| 2004/0152036 A1 | 8/2004 | Abolfathi |
| 2004/0197728 A1 | 10/2004 | Abolfathi et al. |

(Continued)

FOREIGN PATENT DOCUMENTS

DE      10215821      11/2003

OTHER PUBLICATIONS

International Search Report for PCT/US2009/061891, mailed Jun. 22, 2010, 14 pgs.

(Continued)

*Primary Examiner* — John J Wilson
(74) *Attorney, Agent, or Firm* — Squire, Sanders & Dempsey (US) LLP

(57) ABSTRACT

A systematic approach to planning and selection of a dental implant. Models of the patient's dentition, including the gingival and supporting bone structure are analyzed in relation to a model of the dentition that will be replaced by the implant. Based on information collected from a missing tooth (or teeth) model, greater insight can be gained into the functional and aesthetic attributes of the implant best suited for the patient. And from this realization a more informed decision can be made for planning the procedure for installation of the implant for the patient, and selection of the implant, e.g., size, type and orientation of supporting fixture and abutment.

18 Claims, 16 Drawing Sheets

U.S. PATENT DOCUMENTS

| | | | |
|---|---|---|---|
| 2004/0243481 A1 | 12/2004 | Bradbury | |
| 2004/0248066 A1 | 12/2004 | Recigno | |
| 2004/0253562 A1 | 12/2004 | Knopp | |
| 2005/0070782 A1 | 3/2005 | Brodkin | |
| 2005/0159986 A1 | 7/2005 | Breeland et al. | |
| 2006/0172261 A1 | 8/2006 | Garry | |
| 2006/0253212 A1 | 11/2006 | Weber et al. | |
| 2007/0050074 A1 | 3/2007 | Holzner et al. | |
| 2007/0059665 A1 | 3/2007 | Orentlicher et al. | |
| 2007/0134625 A1 | 6/2007 | Leu et al. | |
| 2007/0154866 A1 | 7/2007 | Hall | |
| 2007/0178423 A1 | 8/2007 | Rubbert et al. | |
| 2008/0064008 A1 | 3/2008 | Schmitt | |
| 2008/0090207 A1* | 4/2008 | Rubbert | 433/171 |
| 2008/0153061 A1 | 6/2008 | Marcello | |
| 2008/0154743 A1 | 6/2008 | Holzner et al. | |
| 2009/0162813 A1* | 6/2009 | Glor et al. | 433/196 |

OTHER PUBLICATIONS

"An introduction to the DICOM single-file format", DICOM introduction and free software, downloaded from: www.sph.sc.edu/comd/rorden/dicom, Oct. 20, 2008, 7 pgs.

"Computer based NobelGuide", NobelGuide™ Quick-Guide for Radiologists, downloaded from: www.74.125.95.132/serch?q=cache:A-sgxQ3f47kJ:download.nobelbiocare.com/webcon, Nov. 25, 2008, 2 pgs.

"Discover the latest version", 3D Digital Dental Products & Services, downloaded from: www.materialise.com/materialise/view/en/129846-Discover+the+latest+vision, Oct. 20, 2008, 3 pgs.

Kumar Shah et al., "Treatment Planning for the Single-tooth Implant Restoration-General Considerations and the pretreatment Evaluation", Treatment Evaluation, pp. 827-834 (2008).

Salmassy, "Guided Implant Surgery: Part 1 Model-Based Planning with NobelGuide", Nobel Biocare, 4 pgs. (2006).

"NobelReptace™ Tapered Groovy", procedures and products, Nobel Biocare, 4 pgs. (2007).

"NobelReplace™ Tapered implants", product catalog, Nobel Biocare, 4 pgs. (2005).

"NobelGuide™ perfect planning for perfect teeth", Concept, Nobel Biocare, 6 pgs. (2008).

"Quick Guide-Snappy Abutment™", Impression Technique, Nobel Biocare 2 pgs. (2008).

"Quick Guide-Procera® Esthetic Abutment Selection Kit", Nobel Biocare 1 pg. (2008).

* cited by examiner

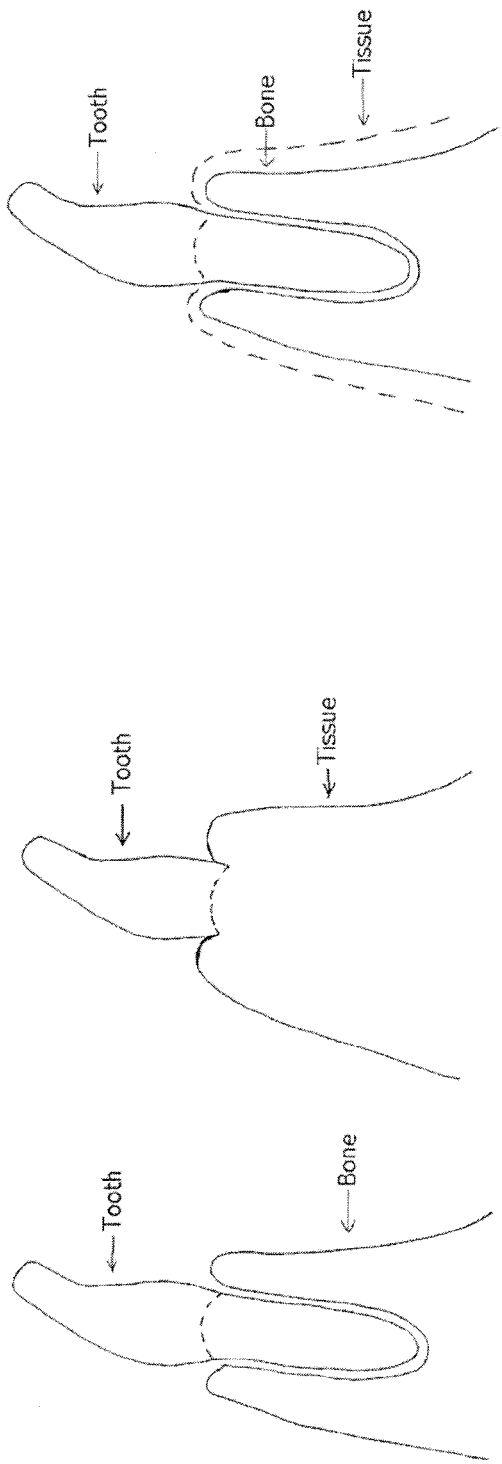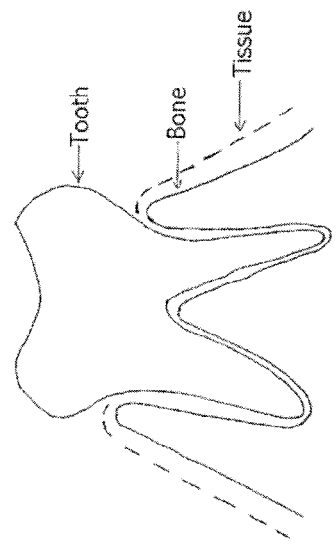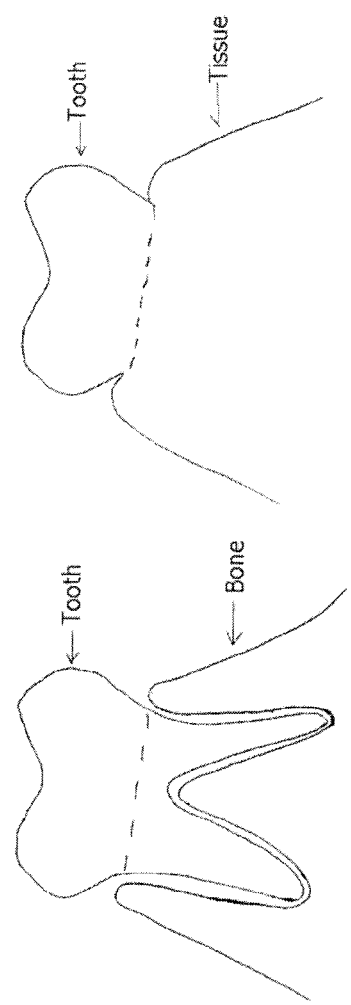
FIG. 4A
FIG. 4B
FIG. 4C
FIG. 4D

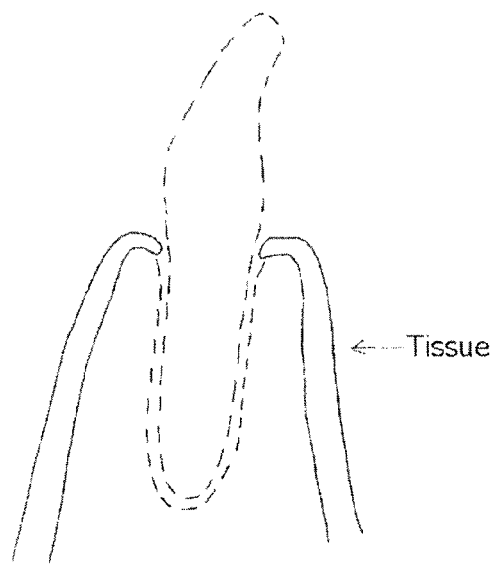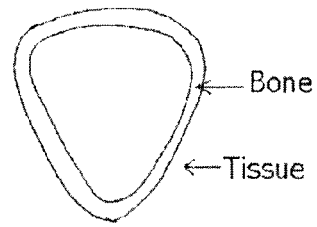
FIG. 5A  FIG. 5B
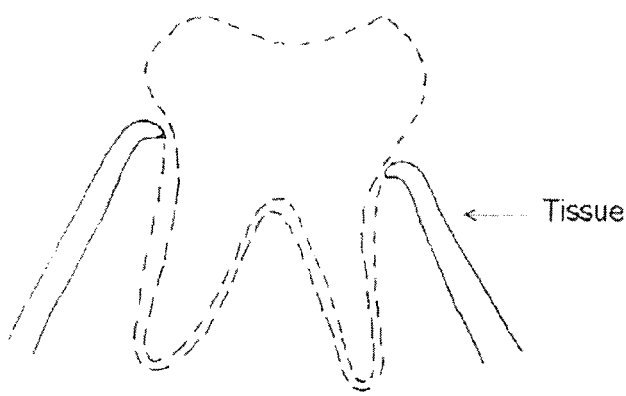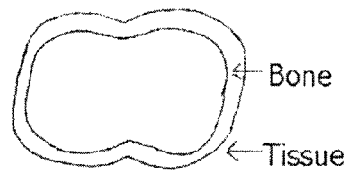
FIG. 6A  FIG. 6B

Maxillary Midline

METHOD FOR TOOTH IMPLANTS

BACKGROUND OF THE INVENTION

1. Field of the Invention

The present invention relates to restorative dentistry; specifically, dental implants relating to restorative and prosthetic dentistry.

2. Background of the Invention

Implants are now a standard way to attach a dental prostheses. One fixture may support a single tooth replacement, usually cemented or screwed atop an abutment. An implant supported bridge (also called a bar or frame) is used when several teeth are missing.

FIGS. 1A and 1B show the basic anatomical structure for a tooth, and a comparison between this structure and the structure most commonly used for a non-removable dental implant. Referring to FIG. 1A, the crown of the tooth includes an outer enamel layer. Beneath the enamel layer is the dentine and then pulp layer. The zone between the crown and the root portion of the tooth is known as the Cemento-Enamel-Junction (CEJ). The gingival tissue or gum surrounds the tooth. FIG. 1B shows the components of a typical single tooth implant juxtaposed with elements of a natural tooth. The implant includes the fixture (called an implant screw in FIG. 1B) and the prosthetic (abutment and crown).

The implant process begins with a determination that a prosthesis is needed to replace a tooth that is no longer capable of carrying chewing loads, no longer capable of supporting an artificial crown, or where the tooth is missing. The restorative dentist may consult with the oral surgeon, trained general dentist, prosthodontist or periodontist to co-treat a patient. Usually, physical models and/or impressions of the patient's jawbones and teeth are made by the restorative dentist at the surgeon's request, and are used as physical aids to treatment planning. If not supplied, the surgeon makes his own or relies upon advanced computer-assisted tomography or a cone beam CAT scan to arrive at a treatment plan.

The area in which the fixture is needed is examined by an oral surgeon who determines where in the patient's jaw a fixture can be safely supported by the bone. Conventional dental x-rays are sometimes relied on to learn if the underlying bone structure appears suitable to support implants and to identify the areas where nerves or other vital anatomical structures are located. There must be bone having a sufficient load-carrying capacity, i.e., a bone having sufficient bone density and adequate depth and width to support normal and transverse loads on the implant. If bone volume or density is inadequate, a bone graft procedure must be considered first.

Unaided manual preparation of a jaw for fixtures supporting prosthesis is challenging, because of the difficulty in estimating positions and angles accurately by the naked eye, within a deep hole of small diameter in a patient's mouth. Even if the work is being done by an experienced dentist or oral surgeon, chances for location, angular or orientation errors are great. For this reasons, drill guides are needed to assist with locating not only the proper drill depth, but entry angle of the drill. Positioning or depth indicators have also been developed to assist with obtaining the appropriate depth and orientation of the hole that will receive the fixture. This part of the process, however, is largely if not wholly controlled by the oral surgeon's determination of how to best hold the fixture in the existing bone, avoiding nerve endings, etc. In other words, the oral surgeon's selection of the type and size of the hole needed, the corresponding fixture screw size, its pitch, diameter, and orientation is not also constrained or a function of the patient's bite or the bite registration, the external loading on the prosthesis for the patient's particular mouth, e.g., the orientation of the adjacent teeth or how they will ultimately function in connection with the adjacent prosthesis, or the nature of the soft tissue surrounding the fixture sight. The oral surgeon drills and places the fixture simply based on the location of bone capable of safely supporting the fixture.

A custom drill guide is now often created to help guide the oral surgeon's drill. Cone Beam technology is used to capture an enhanced view of the upper and lower jaw region of a patient's head. The resulting imagery can show the bone structure and teeth in detail as well as the soft tissues. Using specially designed software that aids in predefining appropriate fixture locations, the Cone Beam data can be used to create another set of data defining the location, orientation, and depth of each cavity to be prepared. From this, with use of a numerically controlled drilling tool, a patient- and case-customized drill guide or surgical guide is constructed. When properly mounted in the patient's mouth, guided holes in this unit align the drilling tool for its use in creating each predefined fixture cavity. Each fixture is then inserted and moved into its permanent location.

After installation of a fixture screw, the implant planning and installation can vary, depending on how long a delay (of up to six months) is allowed for accommodation of the fixture(s) by the bone of the jaw. Some fixture manufacturers recommend loading fixtures immediately, others do not. If a healing delay is to be observed, a healing abutment or a cover screw—a metal extension washer with a domelike-top—is fastened to each fixture by a screw in the threaded hole of the fixture, and the gum flesh is sutured over the abutment.

On successful completion of the foregoing fixture procedure, the patient returns to the Dentist for the later process steps. To install the prosthesis, tissue over the fixture is reopened using a knife or a punch. The healing abutment or the cover screw is removed from the fixtures to reveal the surfaces on which the frame's attachment points will rest. Dental impressions are made of upper and lower jaws using transfer metal copings that attach to the fixture level of the implant. Molds (positive models of the jaws) are made from these impressions, in a traditional procedure duplicating the position of the implants, the soft tissue and the natural teeth. The dental impression or physical molds after being shipped to a dental laboratory are used to build up a prosthesis, in a traditional highly labor-intensive process demanding high accuracy, skill level and long experience for good results.

Thus, traditional prosthesis planning begins after the fixture is installed, not at the beginning, before any surgery has taken place. The traditional process may be likened to that of a house built in an ad-hoc fashion. The ground is excavated and cement poured to create a supporting formwork for a building before deciding what type of building will be supported by the basement, the environmental conditions that the building must withstand, or how the building will sit relative to adjacent architecture. It would be preferred to arrive at a whole design of the integrated prosthesis (fixture, abutment and crown) from the beginning, before any surgery has taken place so that the best implant for the job can be fashioned. In order to do so, the collective sum of the knowledge that goes into each step of creating and installing a prosthesis should be considered.

Other suggestions for implant planning and selection, and related concepts are described in U.S. Pub. No. 2007/0154866, U.S. Pat. No. 7,322,824 and U.S. Pub. No. 2008/0153061

In view of the above, it will be appreciated that today's typical protocol for preparation of the mouth for, and placement of, dental implants involves the following considerations:

a) The human jawbone is highly variable in thickness and density from location to location, and varies from person to person. Thus, for a given individual's jaw, certain implant locations are preferable to others because of bone strength variations.

b) For implant attachment strength, the optimal direction at which the fixture should pass into the bone varies from one jaw location to another, and bone configurations are different from person to person. If the hole in the bone is drilled at an incorrect location and/or angle, the tip of the fixture may pass through the bone and out the far side, weakening its attachment strength and in some instances compromising the integrity of the entire fixture. Protruding fixture tips also raise patient objections on cosmetic grounds.

c) Poor placement of fixtures can be a source of problems in installing and using a prosthesis. If fixtures exit the jaw unparallel with one another it may be more difficult to align the prosthesis to the fixtures properly. In addition, when fixture axes are far from parallel, biting forces will translate from purely compressive force to bending force more likely to fracture the bone, the fixture itself or the prosthetic screws holding the prosthesis to the fixtures.

The known art for the fixture process usually includes installing a titanium screw, installing an abutment, and then installing a corresponding crown atop the abutment. Safety and aesthetics are usually considered during this process (as noted above), but due to a lack of an available systematic analysis of the overall restorative device functions after implantation, the fixture may not function as intended. This may lead to subsequent return trips to the restorative dentist or surgeon replacement of crowns or repair of the supporting jaw due to extensive bone loss, infections, etc.

It would be preferred to have answers to questions such as the functional aspect of the final implant restoration from the implant tip representing the root tip of the natural tooth to the cusp tip of the fabricated crown and the final occlusion and how this effects proper placement of the implant, before the implant is placed in the mouth. For example, how much pressure is being placed on the bone-implant interface? Implant loads from chewing and parafunction can exceed the physio biomechanic tolerance of the implant bone interface and/or the titanium material itself, causing failure. This can be a failure of the implant itself (fracture) or bone loss, or a "melting" or resorption of the surrounding bone.

SUMMARY OF THE INVENTION

The invention relates to aspects of dental implant planning and selection. The restorative dentist should decide what type of prosthesis will be fabricated. Only then can the specific fixture requirements including number, length, diameter, and thread pitch be determined. In other words, the case should be reverse engineered by the restoring dentist, prior to any surgery.

According to one aspect the invention addresses piecemeal or ad-hoc selection and planning. Unlike current approaches for installing implants, where each step is performed separately, without foreseeing what will be built upon a previous element, the fixture screw is selected and planned without knowing what kind of abutment will be put on, an abutment is selected or custom designed without knowing what kind of crown or bridge is built and put on, etc. In accordance with the foregoing objectives there is a process in which each element's role in the finished product is realized before any layer is put in place. A modeled, reverse engineered dentition based on patient data can provide the missing information.

A systematic approach includes extracting the untreated anatomic model, which includes teeth, root, jaw bones and tissue from patient data. This information is then used to create a treated anatomic model, which includes reverse engineering the missing tooth or teeth, based on the root position and angulation, jaw bones-types and density modeled gingival tissues and adjacent tooth structures if present, all obtained from the patient as a comprehensive set of data. After this information is obtained, answers to such questions as what type of titanium screw is proper, screw positions and orientations, screw depth, the abutment type, how should the tissue be punched and modeled after healing, and how should the crowns and bridges be installed above the abutment can be more accurately answered.

According to another aspect, a method provides, in a systematic manner, what has in many cases been a product of skill and experience in restorative dentistry. Rather than rely on the collective expertise and cross-specializations of the various specialists involved in implant planning and selection, where each process has many variables, the idealized solution can be presented to everyone involved in the process. This may be referred to as a reverse engineering solution. By analogy, this concept replaces the house building plan where the foundation is built before knowing what is required of the structure that will be supported by the foundation with an integrated house plan in which the foundation and structure supported by the foundation are designed together, starting with the finished product. Hence, in one respect the invention presents a methodology in which the final result of the implant process, based on the natural features of a healthy tooth, are understood for the specific condition being treated, and before any steps have been taken.

A missing tooth model is, in one respect, the integrated final house design that shows what the foundation will support with respect to the house analogy. In a preferred embodiment a software tool is used to construct a missing tooth in a patient mouth model, as if the patient had never lost the tooth. This missing tooth model enables the consulting dentist, restoration specialist, and/or oral surgeon to realize how the final product is intended to function and how it will look. Some aspects of this model include an accurate tissue punch modeling capability, which produces a gum line that reflects the gum line and the emergence profile of a healthy natural tooth. The model may also include the capability of accurately modeling the gingival tissue after the implant has been set, and the corresponding supporting abutment design that will result in an emergence profile for the implant that can be indistinguishable from adjacent, natural teeth.

One aspect of the invention is model-based processes that lead to selection of the implant components, surgical guide and/or related implant protocol or part manufacture. According to this aspect of the invention, some of the methods of implant planning and selection include the step of "reverse engineering the tooth" or "reverse engineering the missing tooth". This term is defined as the step of predicting, calculating or modeling the functional and aesthetic aspects of a natural tooth, as if it were not missing from the patient's mouth. Thus, the "reverse engineering the tooth" step includes modifying the patient mouth model to include a natural, missing tooth at the location(s) where the implant is intended. A implant, tissue punch, surgical guide, abutments (healing, temporary and/or final) and crown may then be prescribed, described, defined or manufactured in accordance with the attributes of this missing tooth so that the final implant can possess the most similar functional and aesthetic features as possible to that predicted, calculated or modeled for the missing tooth in the "reverse engineering the tooth" step.

According to another aspect of the invention, a software-based analytic model includes, or is adapted as a design tool for predicting the biomechanical properties of the patient's mouth, including the reverse-engineered missing tooth. For example, the model may be used to perform a rigid body loads analysis, or a more detailed stress/strain analysis using Finite Elements or another theoretical approach for computing coupled, biomechanical loading among anatomic structure. The model may further allow the re-shaping or reconfiguring of a missing tooth and then evaluating whether this would be the configuration of a healthy, natural tooth, as if the patient were not missing the tooth. In one respect, the aspects of the analytic model The principles of invention includes preparing and sending models of the reverse engineered tooth, and associated mouth model, using such a model to evaluate alternatives and providing recommendations/comments on a procedure to be followed. It is contemplated that the invention can be used in at least the following situations. A restorative dentist can prepare a three-dimensional model including the reverse engineered tooth. This model may then be transmitted to the oral surgeon for consultation on the type of dentition properties needed in the fixture, and whether the patient's supporting jaw can accept the fixture as planned or to request alternatives. In another example, the restorative dentist or oral surgeon can send a copy of the mouth model, or a portion thereof to a manufacturer for specifying instructions/needs in a fixture screw, abutment or crown.

In accordance with one or more of the foregoing principles of invention, the following additional aspects of invention will be appreciated in light of the disclosure.

According to one embodiment, a method for planning and selection of an implant for a patient includes the steps of providing a patient mouth model, the model missing a tooth; reverse engineering the missing tooth; and planning a dental implant based on functional and aesthetic attributes determined from the reverse engineered missing tooth.

According to another embodiment, a method for installing a dental implant includes obtaining data about a patient's mouth; making an analytic model of the patient's mouth using the data; incorporating into the analytic model a dental prosthesis model, the dental prosthesis model including a representation of the functional and cosmetic attributes of at least a crown, abutment and fixture of the dental prosthesis; selecting an implant protocol on the basis of at least the functional and cosmetic requirements for the fixture, crown and abutment predicted by the analytic model; and installing the dental implant consistent with the implant protocol.

According to another embodiment, a method for planning surgery, includes the steps of providing a patient-specific mouth model, the patient-specific mouth model being adapted for predicting interface loads on a candidate implant as a function of at least the external loading on a modeled, natural tooth supported by a modeled root engaged with a model of the patient's supporting bone; and based at least on data informative of the patient's anatomical structure for supporting a dentition and the predicted interface loads, planning the surgery for installation of the implant.

According to another embodiment, a method for selecting a dental implant includes the steps of providing a predictive model of the dental implant based on a patient-specific mouth model, the mouth model being adapted for representing the anatomical structure for supporting the implant and the loading on a body representing the dental implant; predicting the loading profile for a model of a natural tooth located at the dental implant intended position; and based on the predicted loading, selecting an implant suitable for reproducing the loading profile.

According to another embodiment, a method for selecting an implant includes providing an analytic model of the mouth; adding a missing tooth model to the mouth model and then predicting the functional and aesthetic properties of the missing tooth; and based on the predicted missing tooth functional and aesthetic properties, selecting the fixture that provides a foundation for mounting an abutment and crown that replicates the missing tooth.

According to another aspect of the invention, a method for drill guide design includes the steps of providing bone scan data and surface scan data, producing a mouth model including a tooth and jawbone model where the tooth crown models are taken from the surface scan data and the jawbone model and tooth root models are derived from the bone scan data, and then designing the drill guide based on the crown surfaces in the model in relation to the modeled root and jawbone. In one embodiment the model is created by superimposing the surface scan data acquired from the polyvinyl impressions of the patient's mouth with the bone scan data acquired from the cone beam CT scan of the patient's head.

According to another embodiment, a method for designing an abutment for an implant intended to be placed at an implant location in a patient's mouth includes the steps of modeling the gingival tissue in the patient's mouth; modeling a tissue punch around the implant; and forming a plurality of abutment surfaces adjacent the modeled tissue including at least a CEJ layer; wherein the plurality of surfaces are shaped so as to reproduce a healed gum line similar to the patient's adjacent teeth. In one embodiment, there are four layers that can be independently designed and manipulated to reproduce the ideal emergence profile of an abutment.

According to another embodiment, a method for designing a frame for an implant intended to be placed at an implant location in a patient's mouth includes the steps of modeling the gingival tissue in the patient's mouth; modeling a tissue punch for the implant; and forming a plurality of surfaces adjacent the modeled tissue including at least a CEJ layer; wherein the plurality of surfaces are shaped so as to reproduce a healed gum line similar to the patient's teeth adjacent. In one embodiment, there are five layers that can be independently designed and manipulated to reproduce a natural tooth.

According to another embodiment, a method for making a patient mouth model includes the steps of providing a bone scan of the mouth; providing a surface scan of the mouth; and constructing a tissue model by subtracting a volume represented by the bone scan from a volume represented in the surface scan.

According to other embodiments of the invention, a dental implant, or portion thereof produced by the one or more of the foregoing methods are provided.

According to other embodiments of the invention, a patient mouth model stored on computer readable medium includes a model of the patient's supporting jaw structure, the patient's dentition, and a model of a tooth missing from the patient's mouth. The tooth model includes a crown and root.

According to other embodiments of the invention, a patient mouth model stored on computer readable medium includes a model of the patient's gingival layer, jawbone and dentition. The model may further include a model of missing tooth adapted for use as a guide for planning and selection of an implant at the missing tooth location.

A systematic approach to implant planning and selection in accordance with the foregoing principles of invention may include computer simulation software based on CAT scan data that allows virtual implant surgical placement based on a barium impregnated prototype of the final prosthesis. This predicts vital anatomy, bone quality, implant characteristics, the need for bone or soft tissue grafting, and maximizing the implant bone surface area for the treatment case creating a high level of predictability. Computer CAD/CAM milled, selective laser sintering, stereo lithography, or other rapid prototyping method based drill guides can be developed for the surgeon to facilitate proper fixture placement based on the final prosthesis occlusion and aesthetics. Treatment planning software can also be used to demonstrate "try-ins" to the patient and practitioners on a computer screen. Digital data from a CAT scan (such as an iCAT or a NewTom) can provide accurate simulations that are easily understood by patients and practitioners. When options have been fully discussed between patient and surgeon, software adapted to practice the methods of the invention can be used to produce precision drill guides and other restorative components.

In accordance with the foregoing objectives, it will be appreciated that aspects of the invention offer benefits to doctors and related health professionals, as well as to the patient. The invention can eliminate the need for significant capital investments, reduce administrative time and coordination, reduce trial and temporary dentures, and reduce the probability of poor outcomes, yielding more profit and less hassle. As for patients, in comparison to existing implant practices, there is less elapsed time, fewer office visits, longer implant durability, better esthetics, less pain, and an appreciable reduction in the overall less costs associated with an implant.

INCORPORATION BY REFERENCE

All publications, patent applications or patents mentioned in this specification are herein incorporated by reference to the same extent as if each individual publication or patent application was specifically and individually indicated to be incorporated by reference.

BRIEF DESCRIPTION OF THE DRAWINGS

The invention, together with further advantages thereof, may best be understood by reference to the following description taken in conjunction with the accompanying drawings in which:

FIG. 2C shows a pair of flow diagrams. The left hand diagram describes the typical steps involved in a conventional approach to implant planning and selection, as will be appreciated. The right hand side shows the steps involved according to aspects of the disclosure. It is possible to arrive at both a significant reduction in the number of steps for, and a simplification to the implant planning and selection process, in addition to the other advantages, as indicated in FIG. 2C The benefits to both doctors and patients will be apparent.

FIG. 4A shows a correlation of scan data where crowns of the same anterior tooth in the scan data is used to correlate the anterior tooth scans from FIGS. 3A and 3B, respectively. FIG. 4B shows the resulting bone, tooth and tissue model derived from a superimposing of the surface scan and bone scan data of FIGS. 3A and 3B.

FIG. 4C shows a correlation of scan data where crowns of the same posterior tooth in the scan data are used to correlate the posterior tooth scans from FIGS. 3C and 3D, respectively. FIG. 4D shows the resulting bone, tooth and tissue model derived from a superimposing of the surface scan with the bone scan data of FIGS. 3C and 3D. This may be accomplished by registering, aligning or overlaying the two sets of data.

FIGS. 5A and 5B show side and top views of a tissue portion for the anterior tooth model.

FIGS. 6A and 6B show side and top views of a tissue portion for the posterior tooth model.

DETAILED DESCRIPTION OF THE INVENTION

The description proceeds as follows. First, processes for constructing an analytic model for a patient's mouth, e.g., upper and lower arches, occlusion, based on patient data, are discussed. Next, methods for reconstructing a missing tooth are included as part of the patient mouth model. The missing tooth model, intended to replicate how a natural, healthy tooth would sit in the mouth and function, forms the basis for planning and selection of the implant. The process for restoration of the dentition is then explained, which is based on the information obtained from analysis of the missing tooth model.

Embodiments of the methods of the invention may be practiced in part, or in whole on a work station or personal computer operated by a dental professional, e.g., a treating dentist, or a dentist and assistant health professionals located at a network-based service center. The tools for modeling attributes of a patient's mouth, modeling missing teeth, selecting crown features, abutments, designing a tissue punch, etc. (as discussed below) may be incorporated into a software suite which includes a graphical user interface, or GUI. One example of a GUI and network-based information system that may be modified to practice methods of the invention is the software tool provided by Simplant software. See http://www.materialise.com/materialise/view/en/129846-Discover+the+latest+version.html (downloaded on Oct. 20, 2008).

Many of the examples described below make reference to a planning and section system, process and/or apparatus for restoring a missing tooth. It should be understood, however, that the principles set forth in the following examples, and in accordance with the foregoing objectives, also apply to planning and section of an implant supported restorative bridge. Thus, the disclosure is not intended to be limited to restoring only a single tooth. The disclosure is, however, to apply only to restorative dentistry of the implant type, not patient-removable tooth borne prosthetics.

Figure 2A:
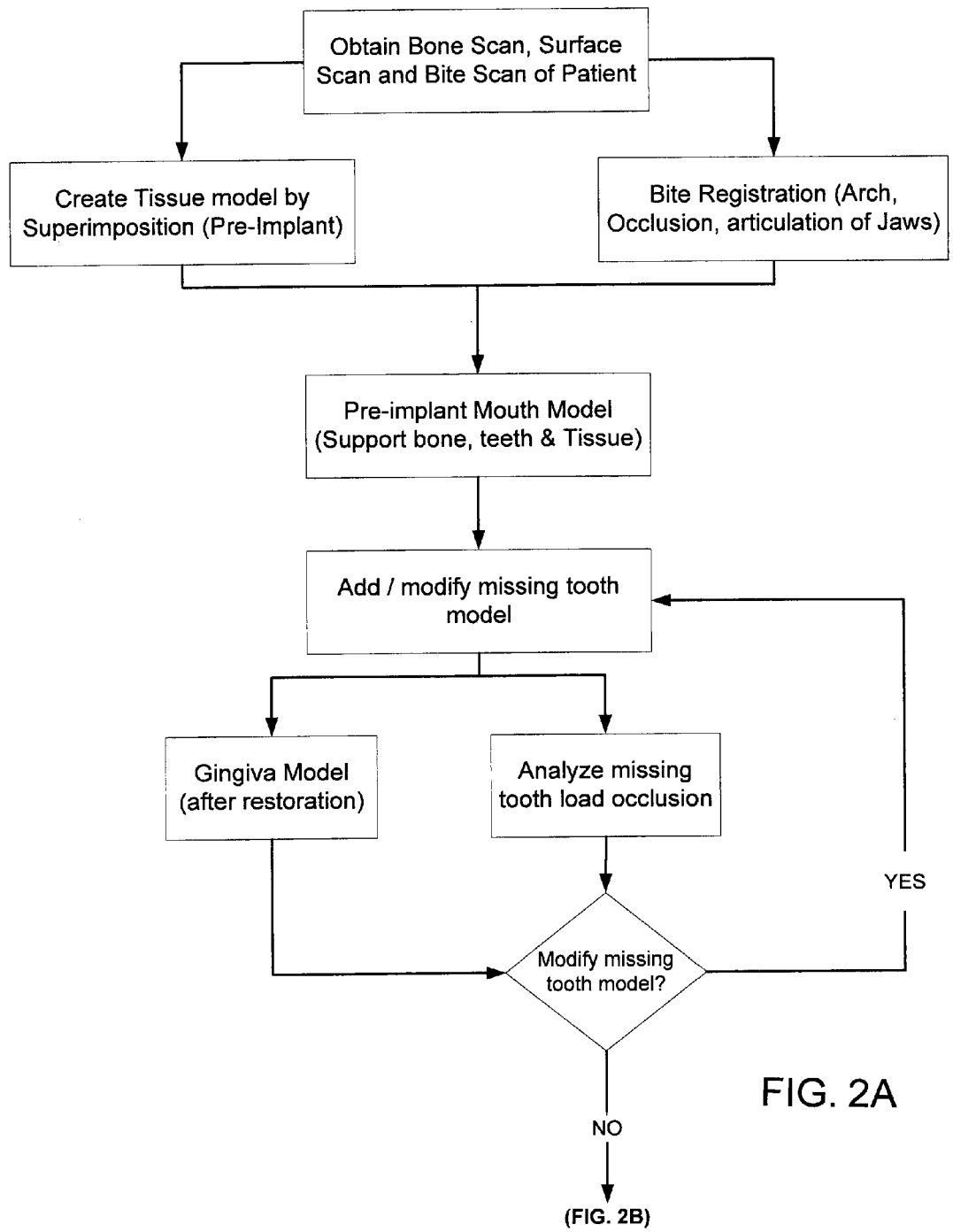
FIGS. 2A-2B are flow diagrams depicting a planning and selection method according to one or more examples set forth in the disclosure. The flow diagrams may be regarded as an implant planning and selection method that includes three phases. The first phase is the construction of the mouth model, pre-implant. The second phase is the construction of a mouth model post-implant. The post-implant model includes a missing tooth model, i.e., the natural tooth, located where the implant is planned. From this representation the attributes of the implant are determined, i.e., abutment, crown and fixture, which is part three of the process. The process for arriving at the missing tooth model and, in essence the features for the implant, may, although may not necessarily be iterative as indicated in FIGS. 2A-2B. The processes depicted in FIGS. 2A-2B may be carried out on a personal computer or workstation. The iterative steps depicted may include additional parameters, other than load vector comparisons, as will be understood from the disclosure.
Figure 2B:
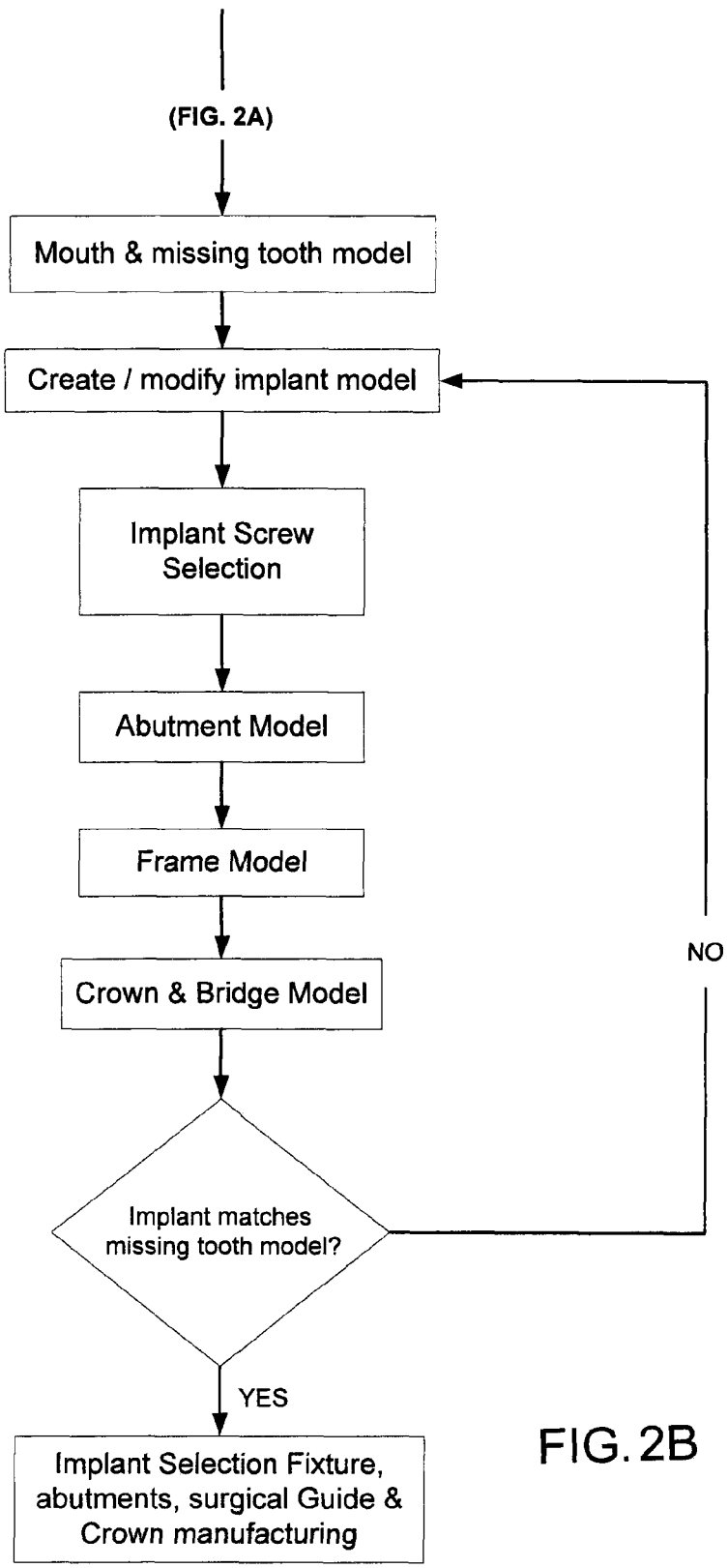

As discussed above, the flow diagram of FIGS. 2A and 2B depict steps according to a process for planning, design and fabrication of an implant. A digital model of the patient's mouth is first constructed. From this model the desired fixture, abutment and crown are selected. This mouth model is constructed using a combination of medical imaging of both the supporting bone structure in the jaw, a surface scan of the patient's mouth, including the tissue and crowns above the gum line, the bite pattern and bite registration between the upper and lower arches in centric relation. From this data a detailed analytic or mathematical model of the bone, teeth and soft tissue may be developed. This model is then used to represent not only the anatomical structure of bone, sinus cavity, vital nerves and soft gingival tissue, but also the structural aspects of the patient's mouth, as a function of the patient's chewing pattern, arch formation and dimensions, loading of individual teeth, tooth spacing, bone density and the like. The model is also used to formulate a desired gingival tissue shape, volume and topography after the implant is inserted into the jaw bone, using a modeling tool of the gingival tissue. FIG. 2A depicts steps involved with making a mouth model and a missing tooth model. FIG. 2B depicts steps involved in making an implant model intended to mimic the predicted functional and aesthetic features form the missing tooth model. In other embodiments one or neither of the processes depicted in FIGS. 2A-2B are iterative.

Information about the patient's bone structure may be obtained using any suitable scanning technology that can produce images of the supporting bone structure beneath the mouth tissue. For example, the images may be obtained using Cone-Beam Computed Tomography (CBCT) based scanning technology known in the art. See e.g., Scarfe et al., *Clinical Applications of Cone-Beam Computed Tomography in Dental Practice*, JCDA, Vol. 72, No. 1 (February 2006). The scanned image data may then be communicated to the dentist using the well known Digital Imaging and Communications in Medicine (DICOM) standard for transfer of medical imaging data. DICOM files can provide detailed, three-dimensional representations of the patient's dentition and supporting jaw bone. Information on the DICOM standard may be found at http://www.sph.sc.edu/comd/rorden/dicom.html (downloaded on Oct. 20, 2008). The DICOM file(s) may be made available over a network. For example, the file(s) may be forwarded to a processing center, preferably over a secure data link. The compressed files may then be remotely accessed and processed securely, e.g. via virtual private network, then forwarded from a server center to the dentist.

A Bone Scan is a scan generated by Cone Beam CT machines such as i-CAT®, iluma®, NewTom®, Galileos, Scanora, ProMax3D, PreXion, etc. This scan may give volumetric data, and usually comes out in a DICOM format. The scan can give information about the jawbone, teeth, nerve and sinus. The data produced by this bone scan will be called "bone scan data", which refers to a three-dimensional representation of anatomic structure produced from, e.g., a series of consecutive two-dimensional image slices having a grayscale representation of different anatomic structure. The bone scan data provides information on the patient's existing crown formations relative to the jawbone, the location of tooth roots, the bone and ligament structure supporting the teeth, and the location of other soft tissue such as nerve endings. These images can inform one of the depth and variation in bone density that can support, or is available for supporting an implant, as well as the adjacent areas of the mouth that are to be avoided, such as nerve endings and/or weak or less dense bone structure.

A Surface Scan is a scan intended to map or trace the surface contours of the patient's dentition. The data, called "surface scan data", is usually stored in polygonal format, e.g. STL or PLY. Surface scan data may be obtained in different ways:

By using an Intra Oral Scan, which scans the dentition intra orally, e.g. 3M Brontes Scanner, Cadent iTereo, Orametrix SureSmile;

By an Impression Scan, where a scan of the dental impressions is made directly. Then the surface scan data is obtained from the impression using an industrial CT scanner, like Flash CT from Hytec; or By a Dental Plaster Scan, where the impression is poured into dental plasters, the dental plasters are then scanned using mainly laser, white light, or mechanical probes. E.g. 3Shape, and Nobel Biocare piccolo/forte.

The surface scan data details the surface contours of the mouth and are also used to construct the mouth model. A surface scan can provide a highly accurate depiction of the gingival tissue, as well as the clinical crown shape, contour and morphology of the teeth above the gum line.

Information on the patient's bite is also obtained for the mouth model. A bite impression may be obtained from an intra-oral scanner, or an industrial 3D CT scanner. Alternatively, a positive dental plaster of the opposing articulated arches may be scanned using a laser, whitelight, infrared or mechanical scanner in order to obtain a bite impression. This bite scan data can be used to obtain most of bite surface information, usually in polygonal format. From this bite scan, a bite registration between the upper and lower arches for the mouth model is constructed representing the centric relation between the two arches and depicting the maximum interdigitation points of contact between these opposing cusps of the Maxillary and Mandibular teeth. From this information, the relative movement of the upper and lower arches during occlusion and function may be determined.

The bone scan and surface scan data of the patient's mouth are combined by superimposing the bone scan data with the surface scan data. For example, the surface contours of the tissue and tooth crowns may be aligned with the image data obtained from the bone scan by matching common crown features. This process is depicted in FIGS. 3-4.

Figure 3A:
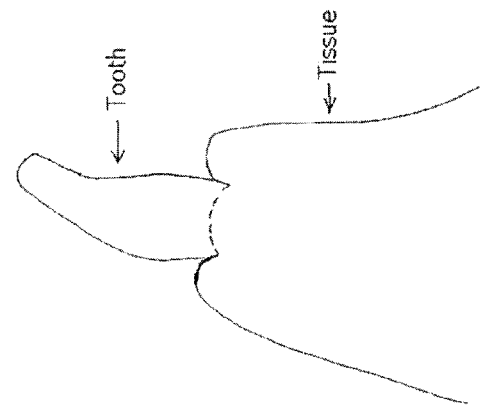
FIG. 3A shows a bone scan for an anterior tooth.
Figure 3B:
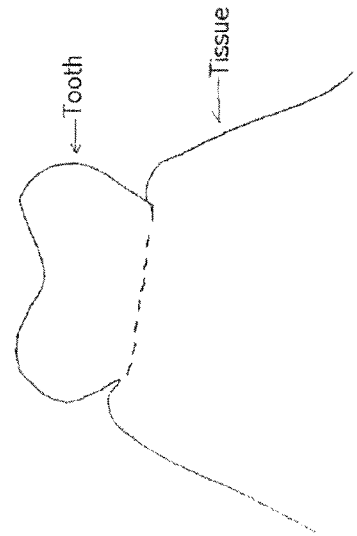
FIG. 3B shows a surface scan for the anterior tooth of FIG. 3A.
Figure 3C:
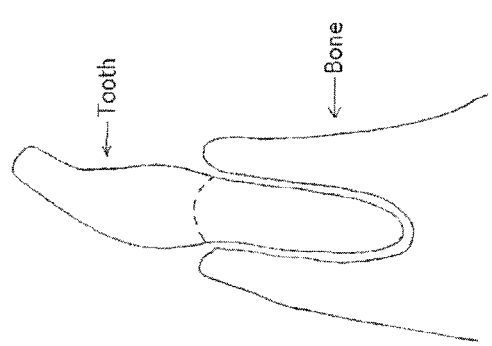
FIG. 3C shows a bone scan for a posterior tooth.
Figure 3D:
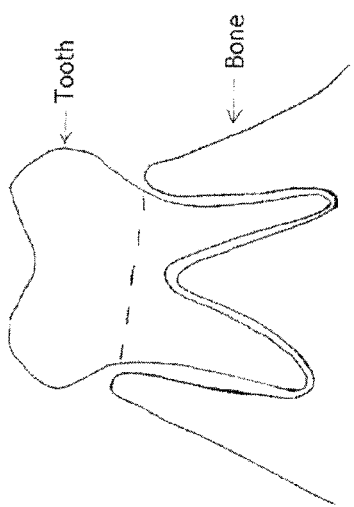
FIG. 3D shows a surface scan for the posterior tooth of FIG. 3C.

FIGS. 3A and 3C show bone scans for an anterior and posterior tooth. FIGS. 3B and 3D show the surface scans for these teeth, respectively. In one embodiment the scan data is matched, aligned or correlated by identifying the matching crowns displayed in each of the images. This process is depicted in FIG. 4A (anterior tooth) and FIG. 4C (posterior tooth). The matching may be done by simple visual inspection of the two images, or by an automated process, e.g., using pattern recognition software. Once this match is found, the two images are superimposed over one another. From this combined set of image data, a tissue model can be extracted. By subtracting the volume data represented between the two scans a tissue model can be created. That is, by differencing the volume occupied by the anatomic structure shown in the bone scan (bone and tooth) from the volume depicted in the surface scan (tissue and tooth crown), a tissue model can be created. As a result, a separate model of the tissue can be combined with the crown and bone data, thereby creating a model of an arch that includes representations of tooth, supporting bone and gingival tissue as separate anatomical structures. This combined model for the anterior and posterior tooth is depicted in FIG. 4B and FIG. 4D, respectively.

One aspect of the mouth model that departs from the known art is this representation of the tissue, both the surface contours and depth of the tissue layer surrounding the jawbone and teeth. By constructing a separate representation of the tissue, e.g., preferably by superimposing the bone scan data with the surface scan data, it is possible to obtain a better aecstatic restoration representing an ideal emergence profile from the tissue than previously thought possible. This tissue model may be used as a basis for modeling the gingival tissue after the implant is placed in the patient's mouth, for planning a customized tissue punch and an abutment suitable for the patient's gum line and topography. The accurate and customized tissue punch will preserve the original papilla, following the tooth contour more closely, and hence enable tissue to heal properly, and most importantly, prevent severe tissue shrinkage after implant placement, which is a common side effect of the current implant process where tissues are either punched using a circular punch or an incision is made and the tissue are completely flapped. In another aspect of the disclosure, a gingival model is used to arrive at the correct tissue punch. For purposes of this description, the term "tissue model" will be used to refer to the model of the patient's tissue before the implant, and the term "gingival model" will be used to refer to the model of the patient's tissue after the restoration. A depiction of a tissue model side view and top view (showing the contours of the tissue with respect to the underlying bone and bone socket, respectively) for the anterior and posterior tooth models of FIGS. 4B and 4D is depicted in solid lines in FIGS. 5A and 5B and FIGS. 6A-6B, respectively.

After superimposing the bone scan data with the surface scan data, the tooth crown surfaces may be separated from the tissue surfaces. In this sense, the tooth crowns refer to the exposed portion of the tooth that was obtained form the surface scan data. In one embodiment the tooth crowns represented in the surface scan data replace the corresponding crowns from the bone scan data. Since the surface scan data tends to be far more accurate, this can lead to a more accurate depiction of the dentition in the mouth model. The crowns may be "stitched" using graphics tools, such as a fusion method, to attach the crown from the surface scan data to the top of the root portion, e.g., the CEJ, from the bone scan data. As such this method will provide more a more accurate tooth model. One particular advantage to forming a mouth model according to this process is enhanced accuracy in drill guide design based on a tooth and jawbone model. The currently known CAD/CAM drill guide processes rely on crown data from a CBCT scan, which is usually far less accurate than crown information obtained from a surface scan. Being less accurate, the drill guide is prone to errors in both drill depth as well as orientation relative to the jawbone since it is based on a relatively inaccurate model of the crowns.

A predictive model of the mouth is constructed. The term "predictive model" (or alternatively, analytic or mathematical model) is intended to mean a model of the mouth that can be used, not only to show volumetric information about the anatomic structures, such as how the tissue is situated relative to the crowns and jawbone, but also how the mouth operates from the standpoint of the biomechanics of the teeth and jawbone when the individual teeth are loaded.

According to one embodiment, the model is used to predict the load vectors on teeth. The load vectors are obtained from resolving vector forces on the surfaces of teeth as determined from the occlusion data and surface contours of the teeth. According to these embodiments, the bone structure, root and crowns of teeth may be modeled as rigid bodies. With such a model the restorative dentist can be quickly informed of the implications of such behavior as the interaction between upper and lower jaws that results in a non-uniform or oblique loading on teeth and the supporting jawbone, the effects of tooth spacing or tilted rotated tooth positions and the resulting atypical loading that results on the supporting bone and teeth. These sometimes, but not always subtle characteristics of a patient's dentition can have a profound impact on the longevity of an implant if the implant planning and selection does not take this factors into account. Indeed, when a restorative dentist does not take these factors into account, as is not uncommon, but rather bases his or her decisions solely on the aesthetics of the implant or safe locations for drilling a hole in the patient's mouth, there is the potential that the patient will need to return once again for an Occlusal adjustment, porcelain chipping and fracture of the fabricated crowns, or corrective surgery including but not limited to bone augmentation procedures and tissue grafting as well.

According to other embodiments, a mouth model may be formulated into a finite element or finite difference representation of the stiffness and strength characteristics of the anatomic structures. Techniques for constructing such a model and modeling a loading on teeth and the jawbone are known. Information used to construct this type of analytic model include stiffness/strength characteristics for different bone types, tooth enamel, periodontal ligament etc. Strength/stiffness characteristics of the anatomic bodies include such parameters as the elastic modulus, yield strength, ultimate strength, elastic/inelastic ranges, failure states and crack propagation characteristics, which may be integrated into a coupled structural stress/strain model. Thus, according to these alternative embodiments, a more precise load distribution over the mouth may be realized since the anatomic structures are no longer assumed to act as rigid bodies.

In other embodiments, a hybrid rigid body and flexible body mouth model may be constructed. For example, the jaw bone and tooth enamel may be modeled as rigid bodies, while the supporting periodontal ligament, for example, coupling the jawbone to the tooth would be represented as a flexible body.

After construction of the analytic model, the attributes of the missing tooth are determined. That is, the size, shape and loading of the missing tooth are included into the model as if it were not missing from the patient's mouth. The determination of the appropriate implant, i.e., size, location, orientation of the fixture, abutment and crown is formulated based on the properties of this modeled tooth. Thus, according to the disclosure a method for restoring a missing tooth is formulated on the basis of the functional and aesthetic features of a modeled missing tooth, prior to any corrective surgery. The fixture screw selection, its location and orientation is not merely determined from the available jawbone structure for supporting an abutment and crown, or the skill and experience of the particular restorative dentist. Rather, it is based on how a natural tooth, including its crown and root, would function in the mouth.

Thus, it will be apparent that a method according to the disclosure departs in several aspects from the known implant planning and selection procedures. According to the disclosure, implant planning and fabrication for the final restoration is completed before any decisions have been reached as to the type of fixture that is needed. As discussed earlier, present implant planning and selection begins with a referral to an oral surgeon who makes a determination of the size and type of fixture screw based on the anatomy of the bone structure, such as bone density and health, the need for restorative surgery of the jawbone, proximity of nerves, etc. Little if any consideration, however, is given for how the implant is expected to function or how the selection of the fixture location, size and orientation might affect the aesthetics or longevity of the implant.

For instance, according to existing procedures, a screw may be placed in the patient's mouth based on the available dense bone or, if there is insufficient bone to support the tooth, the type of screw that can be supported when the jawbone is restored. Considerations such as the spacing between teeth, bite registration and/or chewing pattern and related loading on the implant crown, and/or aesthetics of the finished implant with respect to the adjacent teeth or gum line are not factors typically considered, at least from the standpoint of the known systematic approaches for implant planning and selection. Implant planning and selection today can produce a desired end result when the restorative dentist can draw from years of skill and experience in restorative implants. It is desired to have these skills become part of a systematic approach and not be dependent upon the unique skills of a restorative dentist.

Generally speaking, an oral surgeon is usually, if not only concerned with how to safely drill a hole in a patient's mouth and hold an off-the-shelf fixture in the mouth based on an assumed loading and orientation of the final implant. However, this generalization of how a tooth will function in the mouth often results in later complications, or unacceptable approximations/errors effecting a patient's satisfaction with the finished product. A tooth is not infrequently subjected to oblique loading due to a patient's peculiar bite or chewing patterns, or relationships between the implant and surrounding teeth or other imperfections which over the long run can result in subsequent corrective replacement or surgery. According to the disclosure, these aforementioned ad-hoc measures for design and planning of the fixture screw are replaced by a systematic process for implant planning and selection that establishes the criterion based on an analytic, predictive or mathematical model of the mouth that includes a representation of the missing tooth, as it would naturally sit in the mouth.

According to another aspect of the disclosure, a missing tooth and root model is constructed. This missing tooth model may be used to determine the optimal properties of the implant suited for performing the function required of the missing tooth. Hence, the missing tooth model data (discussed below) can lead to better selection of a screw type, pitch, size, angle of insertion, etc. since the functional aspects of the missing tooth are derived from the unique biomechanics of the patient's mouth. A missing tooth model may be constructed using one or more of the following techniques. During the course of the discussion, the examples make reference to a user software tool that includes an interactive graphical user interface (GUI). Using this tool, a tooth and root may be modeled graphically. That is, the tool is used to generate a proper shape and position in the mouth based on the spacing and location of the supporting bone and adjacent teeth, chewing pattern, spacing between teeth, etc. Further, the shape of the crown may be constructed in relation to the adjacent teeth to achieve a pleasing appearance for the artificial crown. This process may be iterative using GUI methods, such as click and drag, cut and paste, rotation in three-dimensional space, etc.

Figure 7A:
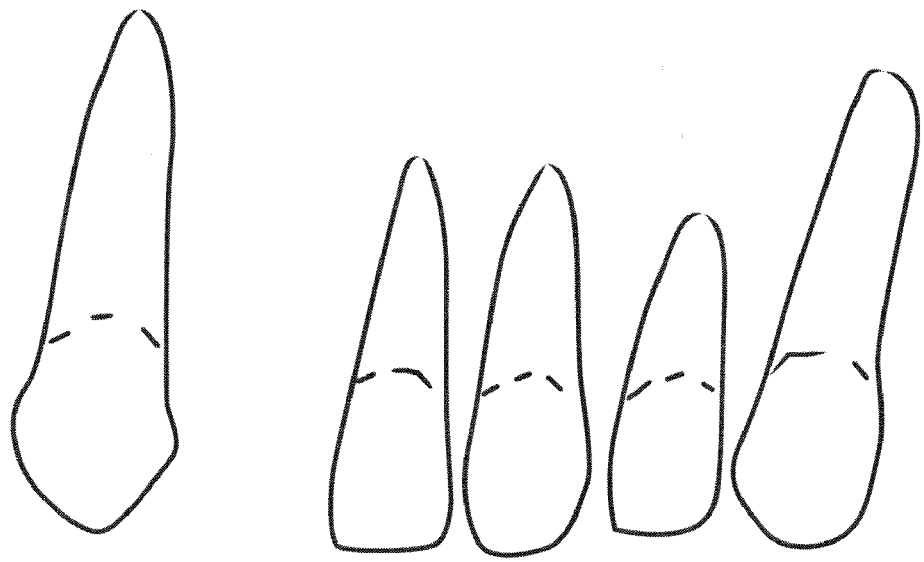
FIGS. 7A-7B depict a missing anterior tooth placement process.
Figure 7B:
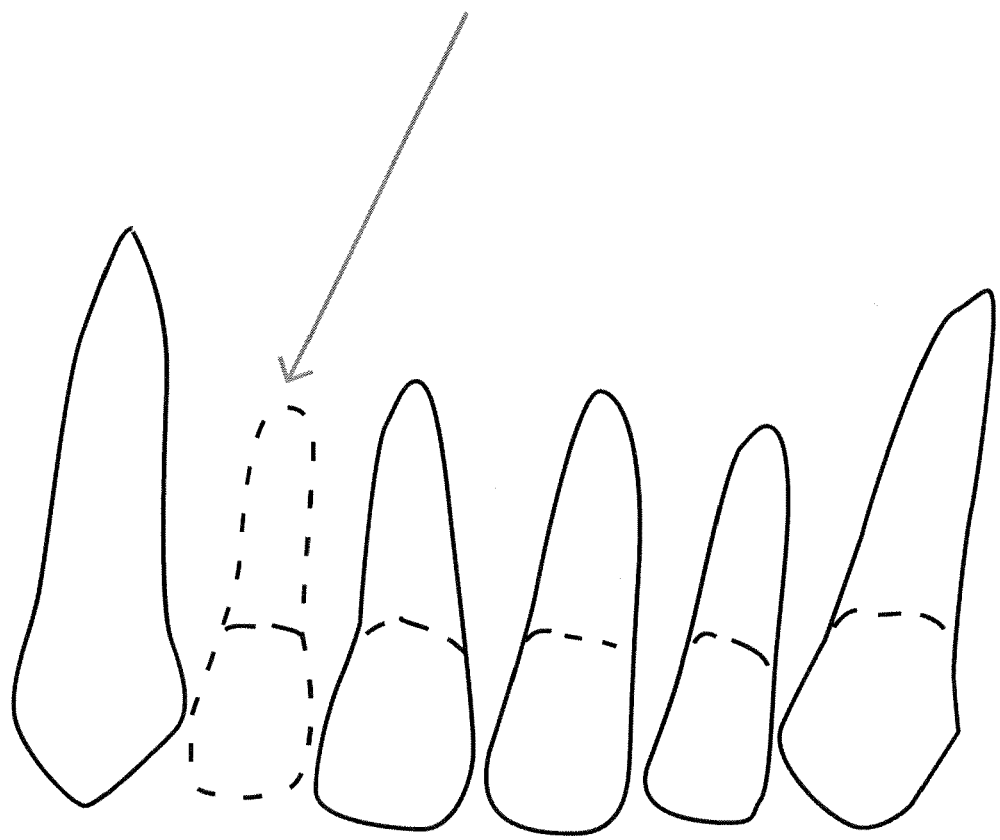

According to one embodiment, selection of the crown and root for the missing tooth may utilize one or more modeling steps. In one embodiment, a three-step process is followed. In the first step, the user selects the stock crown model, which is defined in a local coordinate system, and is translatable, rotatable and resizable along each of three orthogonal axes in the mouth model, i.e., it can be manipulated in three-dimensional space and has nine degrees of freedom (translation, rotation and sizing). The stock crown or tooth types may be based on the location of the missing tooth. In one embodiment, a stock or generic tooth crown is created by mirroring the tooth shape located on the opposing side of the arch, as depicted in FIGS. 7A-7B. The missing tooth crown (FIG. 7B) may be scaled and orientated appropriately according to where it will sit in the mouth and the available space between the adjacent teeth. In general, the shape, size, and orientation of the crown may be selected using one or more of the following criteria:

1. Tooth type
2. Patient age and sex
3. Patient arch characteristics e.g. arch length, curve of spee.
4. The adjacent teeth characteristics
5. The opposing arch characteristics, and occlusion of the mouth.

In steps two and three of the process, a crown and/or root may also be shaped to achieve an optimal bite, natural position or formation relative to the jawbone and/or adjacent teeth, based on factors such as the teeth occlusion. Steps two and three may be utilized to arrive at a customized shape for aesthetic reasons, for functional reasons or both.

Figure 8A:
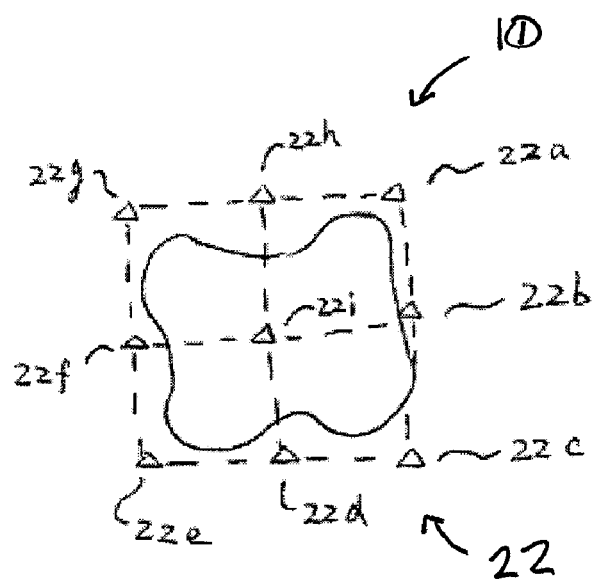
FIGS. 8A and 8B show top and perspective views of a control box used to form a missing tooth for a mouth model.
Figure 8B:
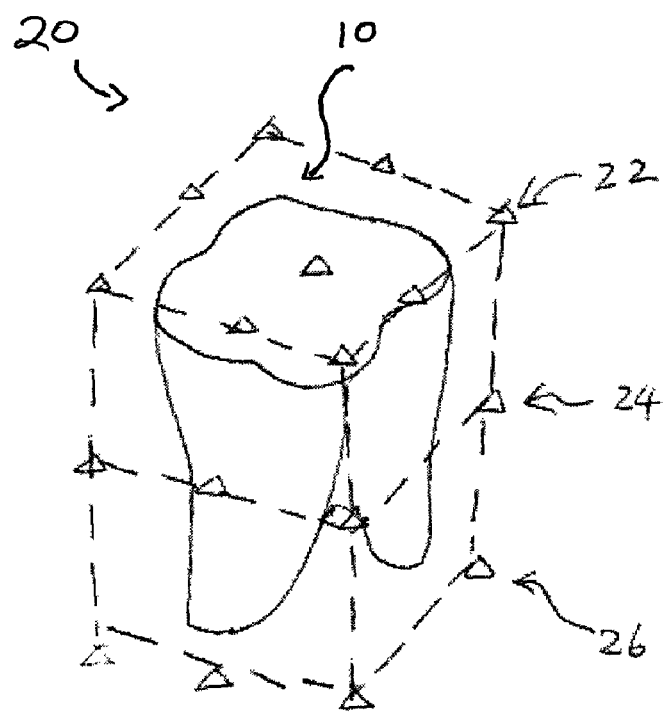

Referring to FIGS. 8A-8B, in some embodiments step two, i.e., the step following the initial sizing and placement of a stock tooth, uses a control box method for the initial shaping of the crown, midlayer and/or root portions of the missing tooth. For example, in FIGS. 8A-8B a control box 20 is used to manipulate the shape of the stock tooth shape (or generic tooth shape) 10 following step one. FIG. 8A shows a top view of the tooth model 10 relative to the control box 20. Shown is the crown portion 12 enveloped by the control box 20 portion for the crown (portion 22). Preferably, the control box 20 has three or more sub-sections corresponding to different portions of the tooth and each sub section has nine associated control points that can be moved relative to each other to create customized surfaces for each section of the tooth.

In FIG. 8B the perspective view of the control box 20 and tooth 10 has a top volume or above-the-gum portion 22 corresponding to the above-the-gum part of the crown, a tissue margin volume layer or portion 24 enveloping the portion of the crown that is covered by the gum tissue, and the bottom or root layer or portion 26 that envelopes the root of the missing tooth. Each section 22, 24, 26 has associated with it nine control points that when moved in three-dimensional space change the portion of the surface associated with that control point. As such, by manipulation of the locations of the control points, a more customized tooth shape can be formed. FIG. 8A shows the nine control points 22a, 22b, 22c, 22d, 22e, 22f, 22g, 22h, 22i for the above-the-gum portion 22. In other embodiments an automatic generation of the above-the-gum portion of the crown, tissue margin layer portion and root portion may be used in the alternative, or in addition to manual control of the control points. The auto-generate embodiment may utilize logic that draws from the spacing information inherent in the mouth model, volumetric or intergeometric constraints so that smooth transitions are generated between the crown, midlayer and root sections, rules for generating the missing tooth based on the one or more of the criteria listed earlier or heuristic rules based on experience and know-how from practice.

Figure 9A:
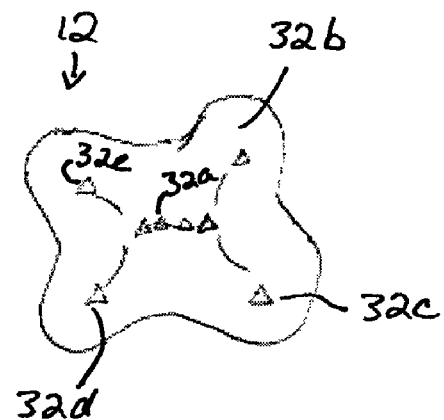
FIGS. 9A and 9B depict dragger nodes for adjusting contours of the missing tooth. The draggers are shown for crown cusps (FIG. 9A), root tip and root function portions (FIG. 9B) of a posterior tooth.
Figure 9B:
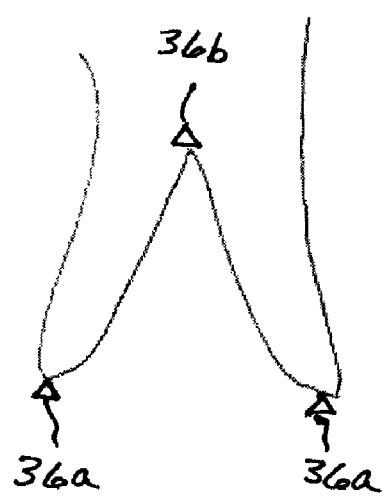

In addition to a manual control box method, the auto-generate embodiments or in the alternative to these methods for shaping/sizing portions of the missing tooth, the tool may also include a capability for dragger local surface features to reshape/resize the missing tooth model. In a preferred embodiment, this is the third step, after steps one and two. For example, in FIG. 9A local dragger 32a corresponding to a central groove, and local draggers 32b, 32c, 32d and 32e corresponding to the four cusps of the biting surface of the crown 12 may be included as part of the crown model portion of the missing tooth model. The local draggers 32 are movable nodes that allow specific portions of the tooth model to be moved in three or two dimensional space to create a customized surface geometry. By including these movable dragger points in the model, the missing tooth model can be conveniently modeled to achieve the desired end product, such as to accommodate a particular registration pattern or occlusion. FIG. 9B shows a corresponding root tip dragger 36a and root function dragger 36b that allows the root portion of the missing tooth model 10 to be re-shaped, e.g., to accommodate or achieve a more realistic fit with the supporting ligament or jaw bone.

According to some embodiments, shapes for the surfaces may also be arrived at by, e.g., iteratively determining the biting surface shape or crown and root body that reduces stress/strain on the enamel or supporting jaw. In these embodiments, a finite element model (FEM) may be utilized to predict the stress/strain distribution for the missing tooth model and associated anatomical structure supporting the missing tooth. A stress distribution is computed for a first body, the contour of this body is then modified to reduce the stress concentrations, then the model re-run to arrive at an improved or optimal shape from the perspective of reducing stress concentrations. Mesh generation algorithms are available that can efficiently regenerate an FEM in order to perform this type of iterative or step-wise analysis on a desktop computer. This technique may also be utilized to identify key load points for implant planning and selection, as described in greater detail, below.

After the missing tooth shape has been selected, or as part of the tooth shape selection process, a cut shape for the tissue punch and the gingival model may be determined for the missing tooth. This modeled cut or punch is part of a gingival model incorporated into the missing tooth model. Unlike existing methods for a tissue punch, the disclosure describes a method for producing a tissue punch that matches the natural contours of the missing tooth. Additionally, the tissue punch accounts for factors such as permitting proper blood flow within the papilla between teeth and the natural position of the missing tooth relative to the gum line. With a properly designed tissue punch, the tissue will heal in such a way as to produce a more natural contour, as planned in the digital design. In the existing methods a tissue punch simply creates a circular hole to accommodate the fixture.

The associated gingival model (i.e., a model of the tissue after implant is installed) is based on the tissue model created earlier. The gingival model is, in general, based on the patient's dentition and tissue geometry relative to the dentition, including the depth of the tissue. Preferably, a software tool is used to enable a user to pre-define and sculpt gingival contours and emergence profiles of teeth for optimal tissue recovery and aesthetics. The gingival model is discussed in greater detail, below, in connection with methods for abutment design.

The mouth model is used to predict load vectors associated with the missing tooth. In contrast to existing methods, load vectors derived from a model intended to mimic the features of a natural tooth and the biomechanics associated with that tooth's proper function should result in a much more informed planning and selection process for the implant. The load vectors are those that can be used to characterize the loading on the crown of the missing tooth, which is a function of its orientation in the mouth, the sharing of the loads with its neighboring teeth, the eccentricities associated with the occlusion or chewing patterns, the abutting surfaces and the type of supporting bone underneath. In some embodiments the load vectors may be represented by resolving a set of two or more vectors acting on the cusps of the missing tooth, while in other embodiments the load vectors can be a product of a more detailed distribution of forces produced from an elastic body analysis.

From this information an improved product and process for planning and selection of an implant, customized for a patient's unique condition, becomes possible. This implant selection also, of course, takes into account the other factors bearing on the proper implant selection and surgical procedure (e.g., location of nerves, depth of the jawbone, etc). The mouth model preferably incorporates these other considerations structures as well. Thus, in some embodiments the mouth model provides the complete anatomic model, which provides all required information, whether an inquiry is made by the consulting dentist, restorative dentist, or oral surgeon.

In some embodiments the load vector analysis may proceed by identifying key loading points, for example:

1. Cusp Fossa.
2. Cusp embrasure
3. Buccalized
4. Lingualized

The Cusp Fossa load vector may be regarded as the primary, or predominate load vector that determines the type, and location of the implant needed. Other selections of primary load vectors and/or secondary load vectors influencing implant selection may be part of the selection process.

According to one method, a load point is determined based on the surface contact between teeth and direction of the biting/grinding between teeth, the occlusion, biting patterns, etc. as determined from the mouth model. From this information the load vectors are determined from a geometric averaging of the individual loading points or rigid body resultant force determination computed from a free body representation of the missing tooth.

Figure 10A:
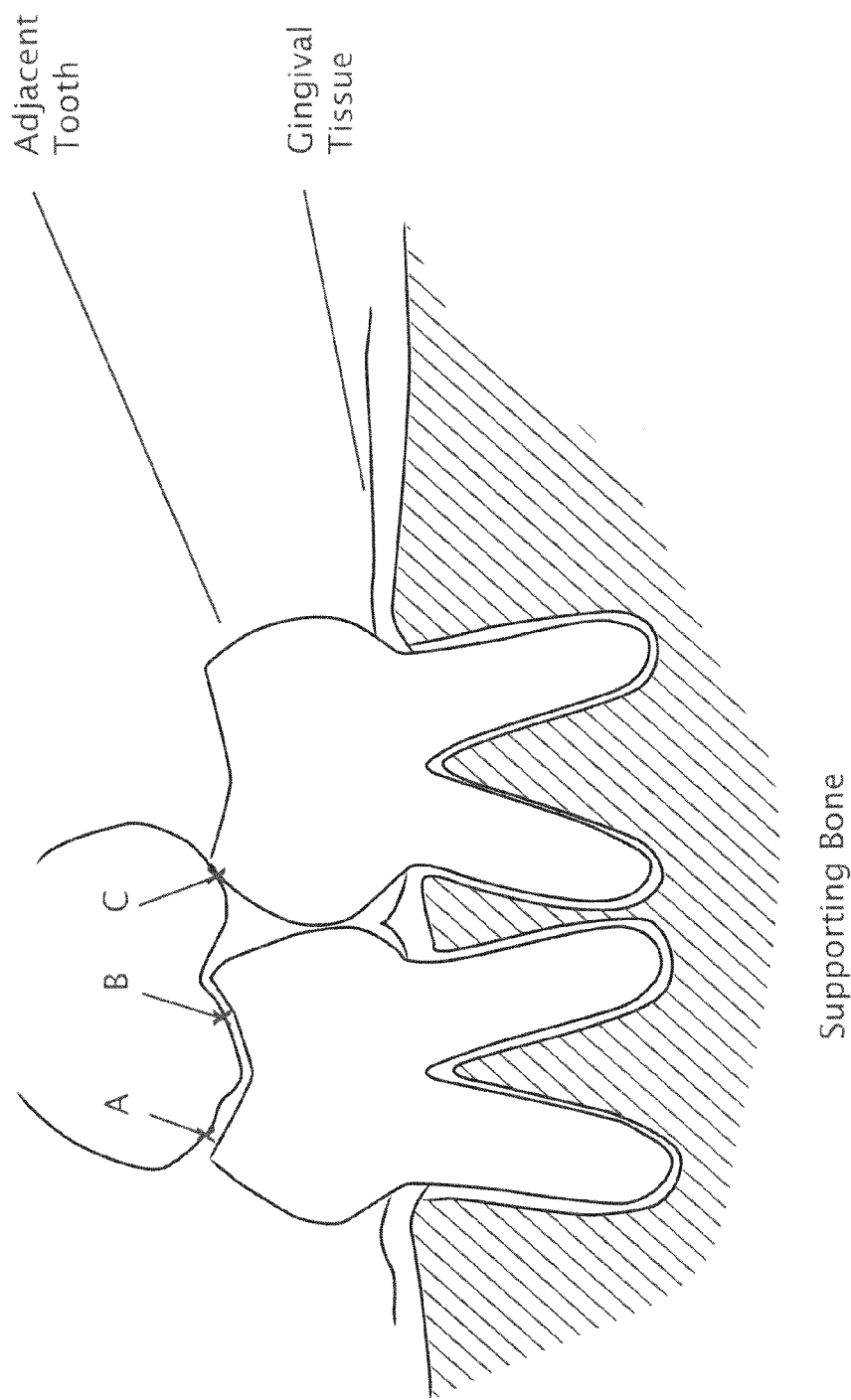
FIG. 10A is a diagram depicting the interaction between the missing tooth, an adjacent tooth and an opposing abutting tooth, as represented in a mouth model.

FIGS. 10A-10D provides an example. FIG. 10A depicts a set of three posterior teeth of the patient's mouth model. The two lower teeth of the lower arch are the missing tooth 10, an adjacent tooth, and an abutting tooth from the upper arch that comes into contact with both the missing tooth 10 and the adjacent tooth according to the patient's occlusion. The contact points between the upper tooth and the two lower teeth are indicated as points A, B and C. The direction of a force vector at points A and B may be determined from an averaging of the pressure applied over a surface of the crown. For instance, the average or net of the surface normal directions of the surfaces of the left cusp in contact with the abutting tooth (location A in FIG. 10A) is the direction of the force vector $C_1$ at point A. From the mouth model the set of equal and opposite forces acting between the abutting tooth, adjacent tooth and the missing tooth model may be solved for using a set of linear equilibrium equations. The net force applied to the lower arch by the abutting tooth in FIG. 10A may be approximated using any known method.

Figure 10B:
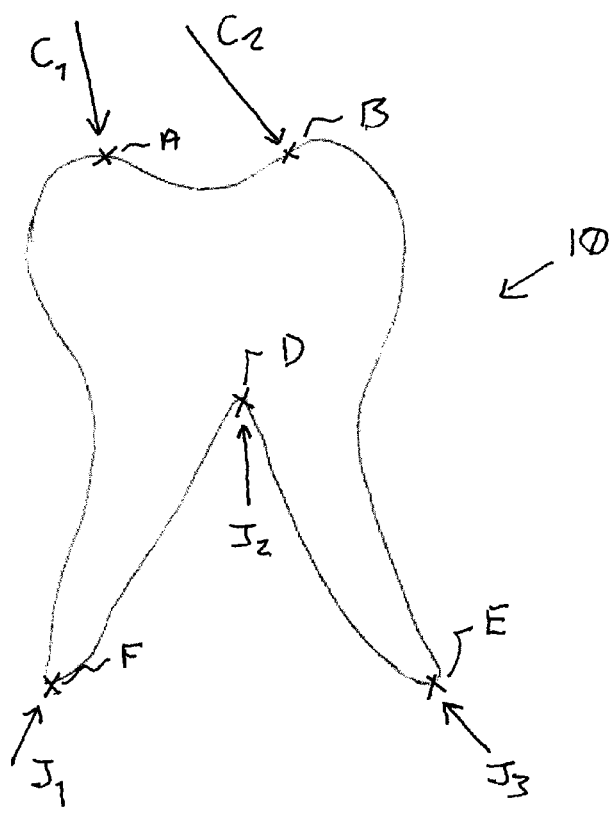
FIG. 10B illustrates a free body diagram for the missing tooth model of FIG. 10A.
Figure 10C:
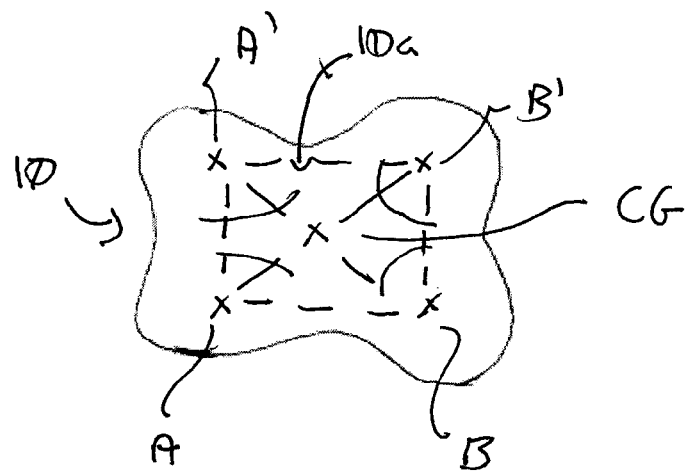
FIGS. 10C and 10D illustrate a resultant force calculation for the missing tooth of FIG. 10A.
Figure 10D:
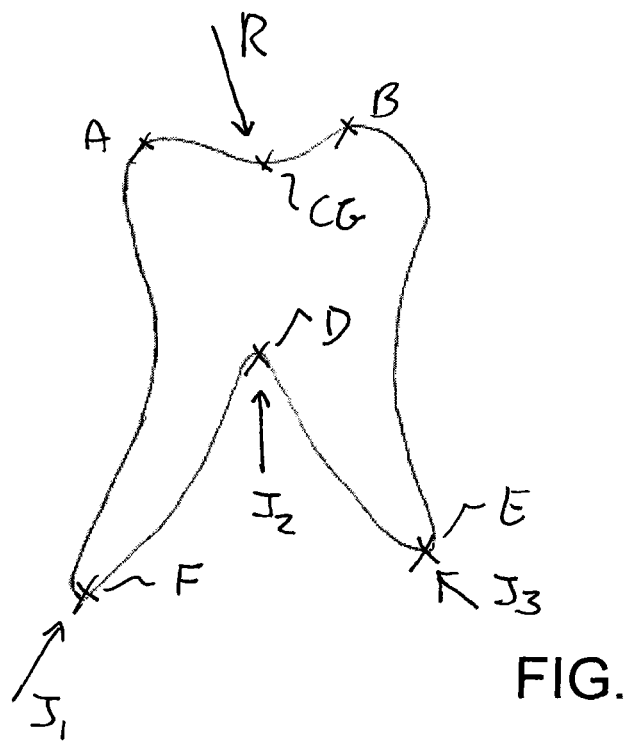

Referring to FIG. 10B, from the solution of the set of linear equations the equilibrating forces acting upon the missing tooth may be found. In this example, the vector forces, i.e., magnitude and direction, acting on the cusps are $C_1$ and $C_2$ and the simplified reaction or equilibrating forces applied by the jawbone at points E, D and F are $J_1$, $J_2$, and $J_3$. FIGS. 10C and 10D show the resultant vector force R of the four cusps A, B, A' and B' with respect to the jawbone force vectors $J_1$, $J_2$, and $J_3$. In the example depicted in FIG. 10C, the location of the point CG for the resultant force vector R is shown. The average or equivalent rigid body resultant force R are CG is found by locating the intersection of the triangles. As shown, the resultant force vector R is skewed significantly, i.e., not normal to the grinding surface of the crown, as might otherwise be assumed. This result may be due to a variety of causes, such as the optimal shape of the crown for the missing tooth, the occlusion, orientation or rotation of teeth, or the spacing between the missing tooth 10 and the adjacent tooth, which can effect the load sharing among the contact surfaces represented as points A, B and C in FIG. 10A. Without the benefit of an accurate model for predicting loads via a missing tooth model, the effects of an eccentric loading of the implant, which reflects a patient's unique condition, can be overlooked.

As will be apparent, the loading of the missing tooth can be quite different from what might be expected during the planning and selection process if only the safe areas for drilling the fixture hole are taken into consideration. The present method, therefore, departs from the known techniques for implant planning and selection because more is taken into consideration than simply the safety of the patient and the availability of dense bone structure to support the tooth. The methods for implant selection and planning according to the disclosure can enable the practitioner to accurately place dental implant fixtures based on the actual interaction of the teeth. This reduces risks of potentially severing certain anatomical structures/nerves in the jaw bones, or otherwise leaving the patient with an uncomfortable sensation when the implant is loaded that may lead to eventual loss of the fixture.

As demonstrated in the above examples, according to some embodiments the mouth model may be constructed as a set of rigid body representations of the tooth crown and root connected to the jawbone structure. In other embodiments, the teeth may be modeled as rigid bodies, while a flexible connection is provided between the supporting jawbone and root, e.g., representing the periodontal ligament or less dense bone structure. According to other embodiments, the load vectors may be arrived at using a finite element model (FEM) representation of the tooth and jaw. This model can produce a stress/strain distribution for the missing tooth model and associated anatomical structure supporting the missing tooth. From this data the stress distributions can be averaged and then used to compute a set of key load vectors for the implant design.

The disclosure therefore provides various methods for reverse engineering a natural bite based on a missing (natural) tooth model. From this model the practitioner can better approximate biomechanical/structural properties for selecting (1) type of fixture; (2) size and length of fixture; (3) fixture orientation; and the (4) fixture depth. In addition, the disclosed methods can facilitate a more intimate fixture manufacturer—consulting or restorative dentist, or oral surgeon ("dentist") relationship that will streamline the process for producing customized and more functionally appropriate implants by sharing information from the missing tooth model.

This manufacturer—consulting or restorative dentist, or oral surgeon relationship may, for example, be facilitated through a third party provider who can transmit some or all of the information about the missing tooth model from the consulting or restorative dentist, or oral surgeon to the manufacturer over a secure, authenticated network connection. In some embodiments, the fixture manufacturer may be provided with essentially a set of characteristic load vectors and two-dimensional drawings illustrating where the fixture is needed and the depth of supporting bone. The load vectors may be defined in terms of a natural tooth, or the corresponding loading points on the fixture, abutment and/or artificial crown. Or the fixture manufacturer may be provided with a three dimensional model that illustrates the forces acting on the missing tooth, or the combined missing tooth and supporting jawbone model (extracted from the mouth model). From this information the manufacturer can fabricate a customized fixture that mimics the biomechanical features of the missing tooth. The service provider may further allow the manufacturer to provide mockups or suggestions to the dentist or surgeon based on his/her assessment of the type of screw or abutment that can be manufactured to meet the functional requirements predicted by the model.

At this point, the practitioner can appreciate the type of fixture that is needed, and the depth and orientation of the hole or osteotomy which will receive the fixture. The foregoing will also inform the practitioner of the nature of the load bearing surfaces for the artificial crown, and the dimensions of the crown. Hence, a decision may be reached as to the type of fixture and crown needed. The other aspect of the implant to consider is the abutment. According to one embodiment, the abutment design is based on the defined load vector.

According to another aspect of the invention, an abutment modeling method is provided. The abutment, which functions as the interface between the crown and implant fixture, is an aspect of the implant which, if not designed properly with regards to the patient's gum line and/or adjacent teeth, can easily distinguish the implant from the adjacent natural teeth, which of course is not desired. According to some embodiments, an implant design therefore includes a design of the emerging tooth profile, i.e., the portion just above the gumline that mimics a natural tooth emerging profile. The design process may be summarized as follows:

1. During formation of the abutment, or crown model, ensure there is enough space to allow for papilla (i.e., the small projection of tissue at the base of the crown) to grow in the space between the teeth, and sufficient space for blood circulation through the papilla;

2. The abutment section should have a smaller diameter as determined from the occlusion table. This consideration reflects the fact that teeth bearing a majority of the grinding/eating load tend to have smaller emergence areas as compared to their crown.

3. Model the abutment as four separate control layers, or abutment modeling controls. These layers may be referred to as the fixture layer, tissue contour, crest height and tissue margin layer.

Layer 1. The fixture layer of the abutment is the defined surface of the abutment bottom layer that will provide an intimate seal between the implant fixture top platform layer and the bottom platform of the abutment. This intimate abutment/implant interface layer seal is necessary to prevent bacterial leakage that can contribute to bone loss around the fixture head.

Layer 2. The tissue contour layer of the abutment defines the geometric shape, thickness and height of the tissue that it supports between the crest of the bone. It is usually flush with the fixture head and the crest of the tissue around the CEJ of the tooth. Various tissue contour layers of the abutments may be necessary for different teeth in the mouth, especially in the cosmetic anterior zone where optimal support for the Interproximal Papilla is required.

Layer 3. The crest height of the abutment layer defines the geometric shape of the abutment, about 0.5 to 1.0 mm below the crest of the tissue around the CEJ of the tooth. This presents optimal support for the tissue as it related to the emergence of the tooth or clinical crown out into the oral cavity.

Layer 4. The abutment margin layer defines either a shoulder or a chamfer margin for the tooth that will be cemented to it. A shoulder margin is usually needed for an all-ceramic crown. The shape of this layer is usually a horizontally geometrically shrunk version of the crest height layer by about 1.5 to 2 mm. A chamfer margin is needed for an oxide ceramic Zirconia or alumina coping that gets porcelain stacked to it to fabricate the final crown.

Figure 1A:
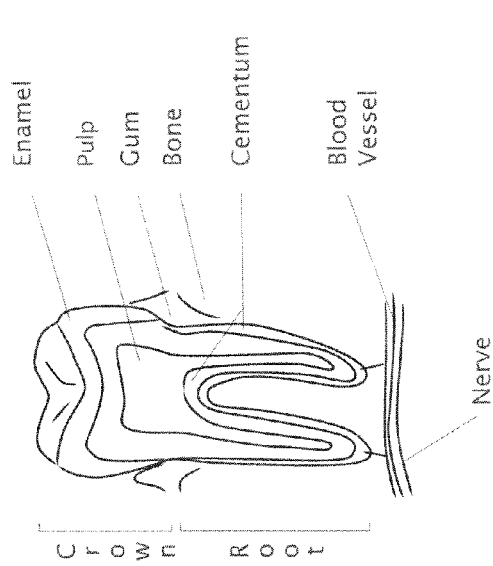
FIGS. 1A and 1B show the basic elements of a natural tooth and an implant.
Figure 1B:
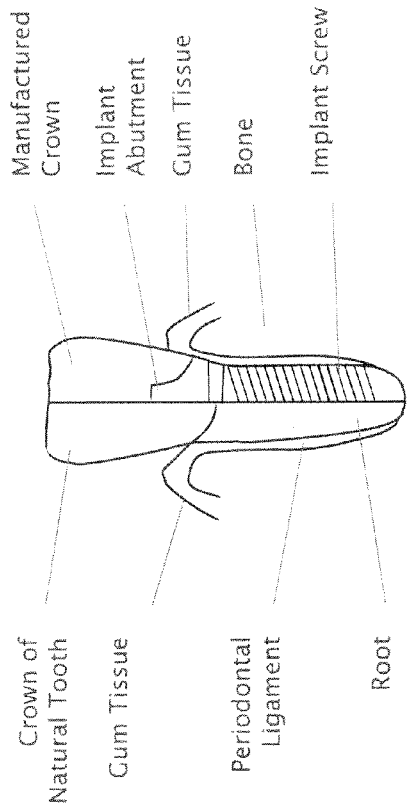
Figure 11A:
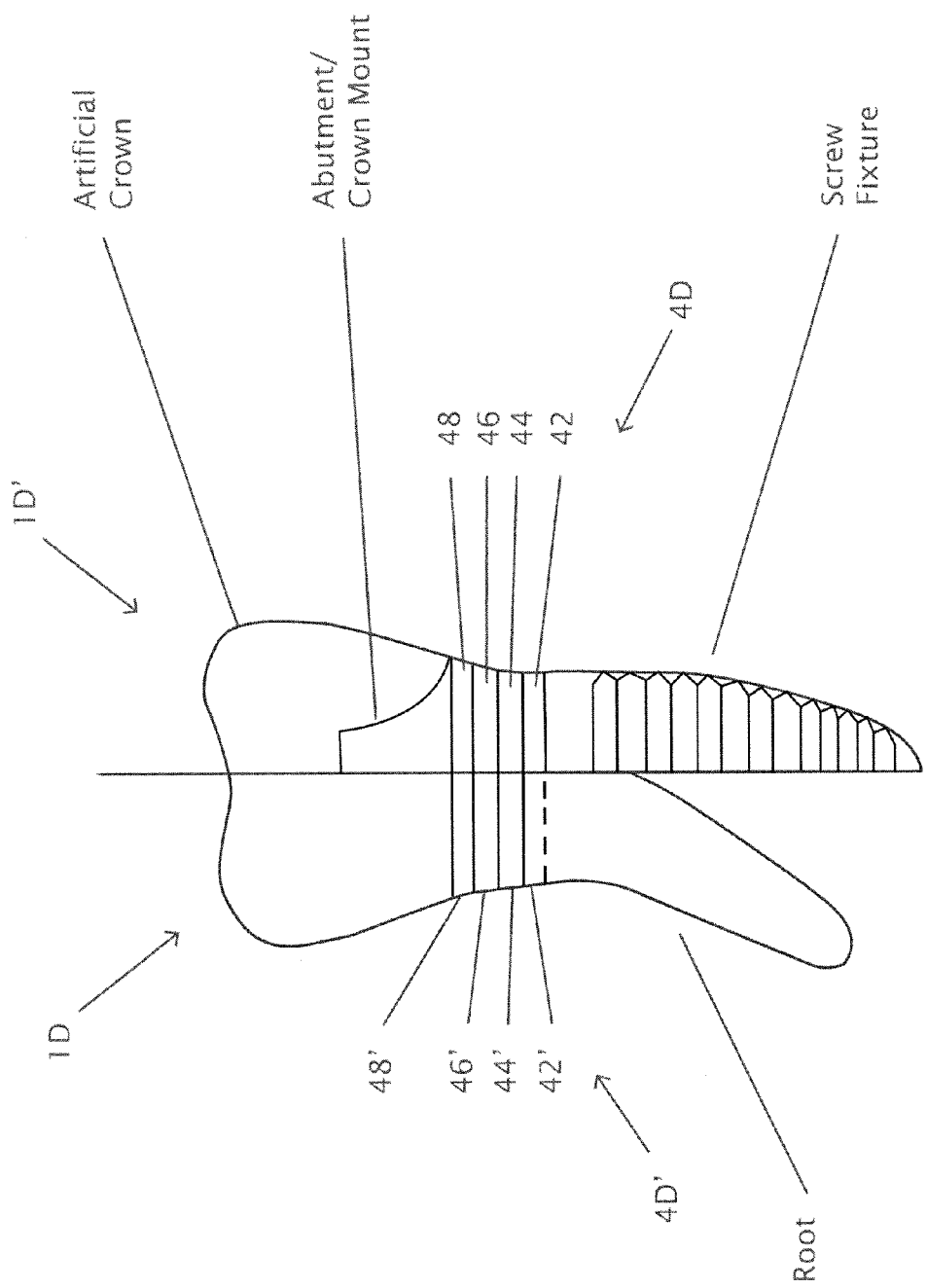
FIG. 11A depicts a partial side view of a missing tooth model juxtaposed with the equivalent implant model and illustrated portions of an abutment portion of the missing tooth model.
Figure 11B:
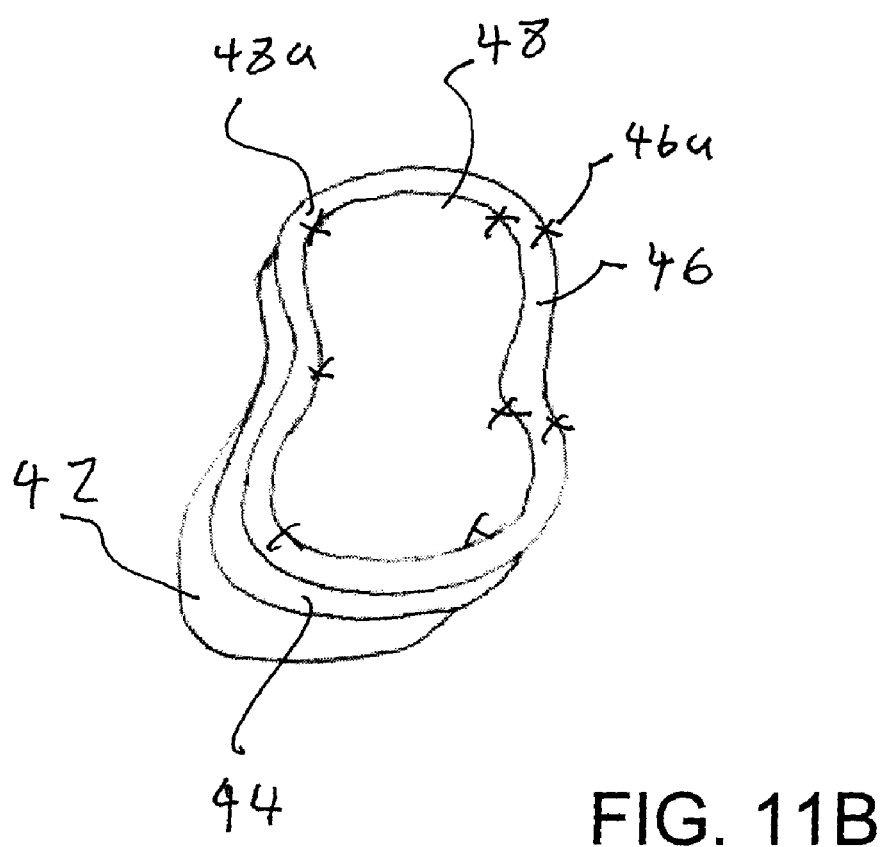
FIG. 11B is a top cross sectional view of the missing tooth model of FIG. 11A illustrating the control points and layers for the abutment portion of the missing tooth model.

FIG. 11A illustrates these four layers in a similar split-view format as FIG. 1B. To the left is the missing tooth model 10 from the mouth model and to the right is the implant 10' equivalent of the missing tooth. The layer between the root and crown (or screw and abutment) is the first layer 42, e.g., fixture layer, followed by the second layer 44, e.g., tissue contour layer, followed by the third layer 46, e.g., crest height layer, and then layer four 48, e.g., the abutment margin layer. Each of these layers may be adjusted independently of each other using a GUI tool to achieve the desired surface for promoting tissue growth that will mimic the gingival surrounding a natural tooth. FIG. 11B shows a top view cross-section of the tooth model 10. As depicted, the layers 42, 44, 46 and 48 may be independently adjusted relative to each other by including control points (in this example six control points such as 46a and 48a) to produce the desired shape for the abutment 40. In some embodiments one or more of the layers 42-48 may include surfaces formed as square, v-shaped or round grooves to promote the desired tissue growth near the abutment. The grooves may be formed to model the Interproximal Papilla, which promotes tissue adherence to the sides of the tooth. According to this embodiment an abutment modeling the Interproximal Papilla and the natural shape of the tooth between crown and root abutment (i.e., looking downward into the tooth socket), in combination with a tissue punch having a cutting surface conforming to this natural shape can produce a healed tissue surrounding the implant that will have a more natural appearance and emergence profile from the gingival tissue than previously thought possible for an implant.

According to one embodiment, there are three types of characteristic abutments that are modeled using the missing tooth model. They are the healing abutment, temporary abutment and final abutment. Each abutment design is based on the gingival model. That is, each of the abutment models are designed for purposes of ultimately forming, as through cooperation of one to the other, a sculptured gingival shape surrounding the final implant/tooth emergence profile.

The four layers (FIGS. 11A-11B) may be constructed using the following guidelines:

For layer 42 the size would be selected based on the size of the implant fixture platform, either internal or external. The platform size would be determined from the earlier load vector analysis, which reveals the type of screw platform needed, orientation of the screw, etc.

For layer 44 the geometry of the corresponding portion of the root form at this layer is reproduced, i.e., layer 44' from FIG. 11A, or the equivalent root forms from adjacent teeth. From this initial sizing, the control points may be used to adjust the dimensions according to the available spacing, areas available for papilla, etc. as discussed earlier.

For layer 46 there may be an upper edge at the upper Y-axis Crest Height of the abutment. The geometric shape of the abutment may be placed 0.5 to 1.0 mm below the crest of the tissue around the CEJ of the tooth. This presents optimal support for the tissue as it related to the emergence of the tooth or clinical crown out into the oral cavity.

For layer 48 the abutment margin layer defines either a shoulder or a chamfer margin for the tooth that will be cemented to it. A shoulder margin is usually needed for an all-ceramic crown. The shape of this layer is usually a horizontally geometrically shrunk version of the crest height layer by 1.5 to 2 mm. A chamfer margin is needed for an oxide ceramic Zirconia or alumina coping that gets porcelain stacked to it to fabricate the final crown. A chamfer margin can be used to orient the crest by, e.g., 5-10% based on the mouth model, adjacent teeth, etc.

EXAMPLES

The following provide examples of methods of design and ultimate manufacture of a healing, temporary and final abutment, temporary and final crowns and bridges, and a surgical guide.

The healing, temporary and final abutment may have a unique design and manufacturing process. For a healing abutment:
1. Define the core of the abutment height and width "#5"—The core should be between "1-7 mm/Height"
2. Insert the axis hole chimney
3. Export a STL file for 3-D printing
For a temporary abutment
1. Define the core of the abutment height and width "#5"—The core should be between "1-7 mm/Height". Then define the body of the abutment shape and height.
2. Insert the axis hole chimney
3. Export a STL file for 3-D printing
For a final abutment:
1. Define the core of the abutment height and width "#5"—The core should be between "1-7 mm/Height". Then define the body of the abutment shape and height.
2. Insert the axis hole chimney
3. Export a STL file for milling either in Titanium or Zirconia Provisional crown and final crown models are based on the tooth modeling and related analysis, as explained earlier. A crown design may be extracted and then later sent to a manufacturer, either as a design drawing or three-dimensional interactive CAD model. The steps for generating the crowns may be as follows:
 i. Load the reverse engineered missing tooth,
 ii. Delete geometry below gingival margin, mostly root model,
 iii. Load abutment model, and
 iv. Generate crown geometry by subtracting abutment model from the tooth model for an all ceramic crown or load the abutment model and add 0.8 mm to 1.2 mm to the entire geometry to design and fabricate a Zirconia or alumina coping.

In the case of a provisional bridge or frame, the design steps may be:
 1. Pick the corresponding designed abutments;
 2. Align and insert the abutment into the tooth model;
 3. Modify and adjust the occlusions with the opposing arch;
 4. Modify and adjust the contacts with the adjacent teeth; and
 5. Define the connector height and width above the gingival crest.

In the case of a final bridge or frame:
 1. Pick the corresponding designed abutments;
 2. Align and insert the abutment into the tooth model;
 3. Modify and adjust the occlusions with the opposing teeth;
 4. Modify and adjust the contacts with the adjacent teeth;
 5. Cutback the crown contour by "1.5-2.0 mm"; and
 6. Define the connector height and width above the gingival crest.
 7. Define embrasure spaces There are three types of surgical guides that may be used. They are a tooth supported, bone supported and mucosa supported surgical guide. A tooth supported model is preferably based on the information obtained from the surface scan, or from the surface information in the mouth model because this data can provide more accurate information about the patient's dentition. A procedure for creating a tooth supported surgical guide may be the following:
 a. Produce the mouth model;
 b. Identify the anchoring tooth from the mouth model;
 b. Create an out shell model of the surgical guide;
 c. Load implant design data;
 d. Insert drill guide cylinders; and
 e. Union cylinder with shell model.

For a bone supported surgical guide, the accuracy of the guide is based on the accuracy of the bone scan data. Therefore, all artifacts of bad scan data should be considered when basing the surgical guide on the supporting jawbone. A process for a bone supported guide may be the following:
 a. Identify the arch;
 b. Create a out shell model of surgical guide:
 c. Load implant design data;
 d. Insert drill guide cylinders; and
 e. Union cylinder with shell model.

For a mucosa supported guide one may use a radiopaque scan prosthesis, which clearly outlines the gingival tissue or a tissue borne removable prosthesis with radiographic markers on the buccal and lingual flanges. A duplicate of the scan prosthesis (visible in CT data) with inserted cylinders, may serve as the basic principle of a mucosa supported Surgical Guide. Production of the scan prosthesis according to the procedure below, and correct positioning of the scan prosthesis in the patient's mouth during the CT scan are important to ensure a successful transfer of the pre-operative treatment plan into surgery. Sufficient vestibular and lingual support are relied on for correct positioning of this guide-type. Additionally, there should be enough supporting surface available in order to use a mucosa-supported surgical guide. The design process for a mucosa supported surgical guide may include the following steps:
 a. Identify the arch;
 b. Load the radio opaque guide;
 c. Load the implant design data;
 d. Superimpose and align b. and c.;
 e. Insert drill guide cylinders; and
 f. Union the cylinder with the shell model.

A radio opaque stent may be generated using the gingival modeling technique described earlier, in combination with CT bone scan data from the mouth model. The radio opaque stent may be fabricated/designed using the following steps:
 1. Identify the arch;
 2. Load gingival model;
 3. Create radio opaque stent shell;
 4. Load CT data;
 5. Load implant design data; and
 6. Superimpose and align data to one.

As mentioned earlier, according to some embodiments a software tool, or suite of software tools capable of running a personal computer is used to perform one or more methods according to the disclosure. The tool or suite may provide a graphical user interface (GUI), menu systems, etc., which can be used to create models, export/import model data, modify a model or design, perform iterative analysis, evaluate potential designs, etc., based on the individual patient mouth model, which includes a digital representations of scanned articulated models of the upper and lower jaws, a tooth replacement design, an abutment design, a gingival model design, an fixture selection based on a patient bone structure, CT scans representing anatomical features i.e. sinus and nerves, measurement tools, digital data of the scanned impressions or stone models. Additionally, an interface is provided so that a treating physician can specify or provide feedback regarding such topics as fixture type, fixture position, a choice on immediate loading or delayed loading, and choice of components (temporary/final or both).

Additionally, in some embodiments the software suite may include tutorial videos, and a web-based user driven tutorial that can allow doctors to review a particular type of treatment he/she is confronted with, e.g. replace a single unit of an incisor or replace with 2 implants, 3 units bridge. The major categories of tutorial video may include
 i. Placement of the Surgical Guide
 ii. Step by Step Drilling Process
 iii. Fixture Insertion
 iv. Removal of the surgical guide
 v. Final Tissue Punching
 vi. Attachment of the following based on Surgery:
  1. Temp Healing Abutment
  2. Temp Abutment
  3. Temp Crown
  4. Final Abutment
  5. Final Crown While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for planning and selection of an implant for a patient, comprising the steps of:
   providing a patient mouth model, the model missing a tooth;
   reverse engineering the missing tooth; and
   planning a dental implant based on functional and aesthetic attributes determined from the reverse engineered missing tooth;
   wherein the reverse engineering the missing tooth step includes the step of modeling an emergence profile and the planning step includes the step of designing an abutment surface based on the modeled emergence profile; and
   wherein the emergence profile is modeled by four independently defined layers, wherein each of the layers are configured using a plurality of associated control points to produce a natural emergence profile and/or to create a healed gingival tissue reflecting a natural gum line.

2. The method of claim 1, wherein the planning step includes designing a surgical guide, fixture, crown, abutment or bridge framework based on the functional and/or aesthetic attributes of the missing tooth.

3. The method of claim 1, further including the step of making the mouth model including the step of superimposing bone scan data with surface scan data.

4. The method of claim 3, wherein the making of the mouth model includes the step of creating a dental crown geometry from the surface scan data and associating the crown geometry with the root geometry obtained from the bone scan data and the planning step includes the step of designing a drill guide from the mouth model.

5. The method of claim 1, wherein the reverse engineering the missing tooth step includes the step of modeling a surface of the missing tooth crown according to the natural features of the missing tooth and the planning step includes the step of selecting an implant based on the modeled crown.

6. The method of claim 1, wherein the reverse engineering the missing tooth step includes the step of forming a missing tooth by at least one of mirroring the natural symmetric tooth on the other side of arch or picking a pre-defined tooth template from a library of teeth.

7. The method of claim 1, wherein the reverse engineering the missing tooth step further includes modeling the gingival tissue adjacent the missing tooth, including the step of modeling a pre-treatment tissue, a punched gingival tissue after implant placement and a gingival tissue after healing.

8. The method of claim 1, wherein the reverse engineering the missing tooth step further includes modeling a pre-treatment gingiva based on a super imposed model of bone scan and surface scan.

9. The method of claim 8, wherein the reverse engineering the missing tooth step further includes modeling a pre-treatment gingiva based on subtracting the bone scan from the surface scan of the super imposed model.

10. The method of claim 1, wherein the reverse engineering the missing tooth step further includes modeling the gingiva of a punched gingiva tissue, and further including shaping the punch based on a natural tooth shape.

11. The method of claim 1, wherein the reverse engineering the missing tooth step includes the step of computing the load vectors on the missing tooth and the planning step includes planning a surgical guide, fixture, abutment, crown, framework, provisional or final bridge based on the computed load vectors.

12. The method of claim 1, wherein the reverse engineering the missing tooth step includes the step of modeling both the missing tooth and the surrounding gingival tissue.

13. The method of claim 1, wherein the reverse engineering the missing tooth step includes the step of designing an abutment surface for the implant that allows the surrounding gingival tissue to form as modeled in a surrounding gingival model.

14. The method of claim 1, wherein the reverse engineering the tooth step includes the step of modeling the crown of the missing tooth based on one or more of the adjacent teeth, one or more teeth on the opposite side of the patent's arch, and the occlusion.

15. The method of claim 1, wherein the reverse engineering the tooth step includes the step of modeling the root of the missing tooth.

16. The method of claim 1, wherein the reverse engineering the tooth step includes the step of shaping the root of the missing tooth based on the bone structure in the supporting jaw.

17. The method of claim 1, wherein the reverse engineering the tooth step includes the step of shaping the cusps or grooves of the missing tooth based on the patient's occlusion and then computing the load vectors resulting from the shaped cusps or grooves to determine the load vectors on the supporting jaw.

18. A method for planning and selection of an implant for a patient, comprising the steps of:
   providing a patient mouth model, the model missing a tooth;
   reverse engineering the missing tooth; and
   planning a dental implant based on functional and aesthetic attributes determined from the reverse engineered missing tooth;
   wherein the reverse engineering the missing tooth step includes the step of modeling an emergence profile, and the planning step includes the step of designing an abutment surface based on the modeled emergence profile; and
   wherein the emergence profile is modeled as a plurality of independently controlled layers, wherein an Interproximal Papilla Thickness is modeled.

* * * * *